United States Patent
Maguire et al.

(10) Patent No.: US 11,932,910 B2
(45) Date of Patent: **\*Mar. 19, 2024**

(54) COMBINATORIAL DNA SCREENING

(71) Applicant: Myriad Women's Health, Inc., South San Francisco, CA (US)

(72) Inventors: Jared Robert Maguire, San Francisco, CA (US); Clement S. Chu, San Francisco, CA (US); Imran Saeedul Haque, San Francisco, CA (US); Eric Andrew Evans, San Bruno, CA (US); Noah Welker, Half Moon Bay, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/383,273

(22) Filed: Jul. 22, 2021

(65) Prior Publication Data

US 2021/0348229 A1 Nov. 11, 2021

Related U.S. Application Data

(63) Continuation of application No. 16/784,761, filed on Feb. 7, 2020, which is a continuation of application No. 15/465,553, filed on Mar. 21, 2017, now Pat. No. 10,597,717.

(60) Provisional application No. 62/311,899, filed on Mar. 22, 2016.

(51) Int. Cl.
*C12Q 1/6874* (2018.01)
*C12Q 1/6818* (2018.01)
*C12Q 1/6886* (2018.01)

(52) U.S. Cl.
CPC ......... *C12Q 1/6886* (2013.01); *C12Q 1/6818* (2013.01); *C12Q 1/6874* (2013.01)

(58) Field of Classification Search
None
See application file for complete search history.

(56) References Cited

U.S. PATENT DOCUMENTS

| | | |
|---|---|---|
| 6,306,597 B1 | 10/2001 | Macevicz |
| 7,115,400 B1 | 10/2006 | Adessi et al. |
| 7,232,656 B2 | 6/2007 | Balasubramanian et al. |
| 7,323,305 B2 | 1/2008 | Leamon et al. |
| 2008/0160580 A1 | 7/2008 | Adessi et al. |
| 2008/0286795 A1 | 11/2008 | Kawashima et al. |
| 2012/0208705 A1 | 8/2012 | Steemers et al. |
| 2013/0225452 A1 | 8/2013 | Pollack et al. |
| 2013/0261019 A1 | 10/2013 | Lin et al. |
| 2014/0342354 A1 | 11/2014 | Evans |
| 2015/0080266 A1 | 3/2015 | Volkmuth et al. |
| 2015/0301058 A1 | 10/2015 | Schettini |
| 2015/0376700 A1 | 12/2015 | Schnall-Levin et al. |
| 2016/0053301 A1 | 2/2016 | Raymond et al. |

FOREIGN PATENT DOCUMENTS

| | | |
|---|---|---|
| WO | WO-2011/103236 A2 | 8/2011 |
| WO | WO-2013/112923 A1 | 8/2013 |
| WO | WO-2014/015084 A2 | 1/2014 |
| WO | 2014151117 | 9/2014 |
| WO | 2016040901 | 3/2016 |

OTHER PUBLICATIONS

Newman et al (Nature Medicine. May 2014. 20(5): 548-554 and Supplementary Information pp. 1-22 (Year: 2014).*
Chan et al Clinical Chemistry. 2013. 59(1): 211-224 (Year: 2013).*
Dawson, et al., "Analysis of Circulating Tumor DNA to Monitor Metastatic Breast Cancer", The New England Journal of Medicine, 368;13, Mar. 28, 2013 (1199-1209 and Supplemental Appendix).
Diehl et al., "Circulating mutant DNA to assess tumor dynamics", Nat Med. Sep. 2008;14(9):985-90. doi: 10.1038/nm.1789. Epub Jul. 31, 2007.
Garcia-Murillas et al., "Mutation tracking in circulating tumor DNA predicts relapse in early breast cancer", Sci Transl Med. Aug. 26, 2015;7(302):302ra133. doi: 10.1126/scitranslmed.aab0021.
Lipson et al., "Circulating tumor DNA analysis as a real-time method for monitoring tumor burden in melanoma patients undergoing treatment with immune checkpoint blockade", J Immunother Cancer. Dec. 16, 2014;2(1):42. doi: 10.1186/s40425-014-0042-0. eCollection 2014.
Woo et al., "Profiling of exome mutations associated with progression of HBV-related hepatocellular carcinoma", PLoS One. Dec. 18, 2014;9(12):e115152. doi: 10.1371/journal.pone.0115152. eCollection 2014.
Wagle et al., "High-throughput detection of actionable genomic alterations in clinical tumor samples by targeted, massively parallel sequencing", Cancer Discovery, 2012, vol. 2, No. 1, pp. 82-93.
Altschul et al., "Basic Local Alignment Search Tool", Journal of Molecular Biology, 1990, pp. 403-410, vol. 215, 1990 Academic Press Limited.
Botezatu et al., "Genetic Analysis of DNA Excreted in Urine: A New Approach for Detecting Specific Genomic DNA Sequences from Cells Dying in an Organism", Clinical Chemistry, vol. 46, No. 8, May 22, 2000, pp. 1078-1084.
Branton et al., "The potential and challenges of nanopore sequencing", Nat. Biotechnol., vol. 26, 2008, pp. 1146-1153.

(Continued)

*Primary Examiner* — Carla J Myers
(74) *Attorney, Agent, or Firm* — Foley & Lardner LLP

(57) ABSTRACT

The present disclosure relates to methods for detecting unique genetic signatures derived from markers such as, for example, mutations, somatic or germ-line, in nucleic acids obtained from biological samples. The sensitivity of the methods provides for detection of mutations associated with a disease, e.g., cancer mutations, or with inherited disease, e.g., an autosomal recessive disease, in a noninvasive manner at ultra-low proportions of sequences carrying mutations to sequences carrying normal, e.g., non-cancer sequences, or a reference sequence, e.g., a human reference genome.

14 Claims, 17 Drawing Sheets

Specification includes a Sequence Listing.

(56) References Cited

OTHER PUBLICATIONS

Browning et al., "Haplotype phasing: Existing methods and new developments", Nat. Rev. Genet., vol. 12, Apr. 1, 2012, pp. 703-714.
Chen et al., "Microsatellite alterations in plasma DNA of small cell lung cancer patients", Nature Medicine, vol. 2, No. 2, Sep. 1996, pp. 1033-1035.
Duncavage et al., "Hybrid Capture and Next-Generation Sequencing Identify Viral Integration Sites from Formalin-Fixed, Paraffin-Embedded Tissue", The Journal of Molecular Diagnostics, May 3, 2011, vol. 13, No. 3, pp. 325-333.
Fan et al., "Noninvasive diagnosis of fetal aneuploidy by shotgun sequencing DNA from maternal blood", PNAS, vol. 105, No. 42, Oct. 21, 2008, pp. 16266-16271.
Fierer et al., "The influence of sex, handedness, and washing on the diversity of hand surface bacteria", Proc. Nat'l Adad. Sci., vol. 105, Nov. 18, 2008, pp. 17,994-17,999.
Gnirke et al., "Solution hybrid selection with ultra-long oligonucleotides for massively parallel targeted sequencing", Nature Biotechnology, vol. 27, No. 2, Feb. 2009, pp. 182-189.
Gudmundsson et al., "Genome-wide association and replication studies identify four variants associated with prostate cancer susceptibility", Nat Genet., vol. 41, No. 10, Oct. 2009, pp. 1122-1126.
Hamady et al., "Error-correcting barcoded primers allow hundreds of samples to by pyrosequenced in multiplex", Nature Methods, vol. 5, No. 3, 2008, pp. 235-237.
Henikoff et al., "Amino acid substitution matrices from protein blocks", Proceedings of the National Academy of Sciences USA, vol. 89, Nov. 1992, pp. 10915-10919.
Higgins et al., "CLUSTAL: a package for performing multiple sequence alignment on a microcomputer," Dec. 15, 1988, Gene, vol. 73, No. 1, pp. 237-244.
Hopp et al., "A Short Polypeptide Marker Sequence Useful for Recombinant Protein Identification and Purification," Bio/Technology, Oct. 1988, vol. 6, pp. 1204-1210.
Horhota et al., "Glycerol nucleoside triphosphates: synthesis and polymerase substrate activities", Organic Letters, Sep. 8, 2006, vol. 8, No. 23, pp. 5345-5347.
International Search Report and Written Opinion issued in corresponding International Application No. PCT/US2017/023482, dated Jul. 27, 2017 (13 pages).
Karlin et al., "Applications and statistics for multiple high-scoring segments in molecular sequences", Proc. Natl. Acad. Sci., vol. 90, Jun. 1993, pp. 5873-5877.

Koide et al., "Fragmentation of cell-free fetal DNA in plasma and urine of pregnant women," Prenatal Diagnosis, vol. 25, No. 7, Jul. 2005, pp. 604-607.
Koren et al., One chromosome, one contig: Complete microbial genomes from long-read sequencing and assembly, Curr. Opin. Microbiol. vol. 23, Dec. 1, 2014, pp. 110-120.
Krishnan et al., Barcodes for DNA Sequencing with guaranteed error correction and capability, Electronics Letter, vol. 47, 2011, pp. 236-237.
Langmead et al., "Ultrafast and memory-efficient alignment of short DNA sequences to the human genome", Genome Biology, vol. 10, Issue 3, Mar. 4, 2009 (10 pages).
Lefrancois et al., Efficient yeast ChiP-Seq using multiplex short-read DNA sequencing, BMC Genomics, vol. 10, 2009, pp. 1-18.
Li et al., "The Sequence Alignment/Map format and SAMtools", Bioinformatics, vol. 25, No. 16, 2009, pp. 2078-2079.
Lo et al., "Presence of fetal DNA in maternal plasma and serum", The Lancet, vol. 350, Aug. 16, 1997, pp. 485-487.
Lutz-Freyermuth et al., "Quantitative determination that one of two potential RNA-binding domains of the A protein component of the U1 small nuclear ribonucleoprotein complex binds with high affinity to stem-loop II of U1 RNA", Proc. Natl Acad. Sci. USA, vol. 87, Aug. 1990, pp. 6393-6397.
Martin et al., "GAP Domains Responsible for Ras p21-Dependent Inhibition of Muscarinic Atrial K+ Channel Currents", Science, vol. 255, No. 5041, Jan. 10, 1992, pp. 192-194.
Mertes et al., "Targeted enrichment of genomic DNA regions for next-generation sequencing", Briefings in Functional Genomics, 2011, vol. 10, No. 6, pp. 374-386.
Metzker, Michael, "Sequencing technologies—the next generation", Nature Reviews, vol. 11, Jan. 2010, pp. 31-46.
Needleman et al., "A General Method Applicable to the Search for Similarities in the Amino Acid Sequence of Two Proteins", J. Mol. Biol., vol. 48, Mar. 28, 1970, pp. 443-453.
Skinner et al., "Use of the Glu-Glu-Phe C-terminal Epitope for Rapid Purification of the Catalytic Domain of Normal and Mutant ras GTPase-activating Proteins", The Journal of Biological Chemistry, vol. 266, No. 22, Aug. 5, 1991, pp. 14163-14166.
Su et al., "Human Urine Contains Small, 150 to 250 Nucleotide-Sized, Soluble DNA Derived from the Circulation and May Be Useful in the Detection of Colorectal Cancer", Journal of Molecular Diagnostics, vol. 6, No. 2, May 2004, pp. 101-107.
Turner et al., "Massively parallel exon capture and library-free resequencing across 16 genomes", Nat. Methods, 6:315-316, 2009.
Voelkerding et al., "Next-Generation Sequencing: From Basic Research to Diagnostics", Clinical Chemistry, vol. 55, No. 4, 2009, pp. 641-659.

* cited by examiner

| condition | normal | cancer | mixture | lower | upper |
|---|---|---|---|---|---|
| mix_0_rep1 | 3406585 | 1 | 2.9355e-07 | 7.4320e-09 | 1.6355e-06 |
| mix_0_rep2 | 3110983 | 1 | 3.2144e-07 | 8.1382e-09 | 1.7910e-06 |
| mix_1e5_rep1 | 3540529 | 18 | 5.0840e-06 | 3.0131e-06 | 8.0348e-06 |
| mix_1e5_rep2 | 3444781 | 30 | 8.7088e-06 | 5.8758e-06 | 1.2432e-05 |

FIG. 6

SEQUENCE LISTING

<160> NUMBER OF SEQ ID NOS: 12

<210> SEQ ID NO 1
<211> LENGTH: 13
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
aatgccatgg ctt                                                        13

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cagtagctct gat                                                        13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gacgtatacg ctt                                                        13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tacggactcg tat                                                        13

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aacgttcgag tcct                                                       14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cacgttacga tgat                                                       14

<210> SEQ ID NO 7
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 7
gctcctagac gtat                                                            14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tatcgagcta gcct                                                            14

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acgtagctga tcagt                                                           15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caggactagc ttact                                                           15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcatcgctag tagat                                                           15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tacgtagtac gcagt                                                           15
```

COMBINATORIAL DNA SCREENING

CROSS-REFERENCE TO RELATED APPLICATIONS

The present application is a continuation of U.S. patent application Ser. No. 16/784,761, filed Feb. 7, 2020, which is a continuation of U.S. patent application Ser. No. 15/465,553, filed Mar. 21, 2017, which claims priority to U.S. Provisional Patent Application Ser. No. 62/311,899, entitled "Combinatorial DNA Screening," filed Mar. 22, 2016.

SEQUENCE LISTING

The instant application contains a Sequence Listing which has been submitted electronically in ASCII format and is hereby incorporated by reference in its entirety. Said ASCII copy, created on Jul. 22, 2021, is named 04268-012US3_SeqListing.txt and is 4 KB in size.

TECHNICAL FIELD

The present disclosure relates to methods for detecting somatic mutations in cell free DNA obtained from biological fluid samples. The sensitivity of the methods provides for detection of mutations associated with a disease, e.g., cancer mutations, or inherited mutations in a fetus in a noninvasive manner at ultra-low proportions of sequences carrying somatic mutations to sequences carrying normal, i.e., non-cancer or wild-type sequences.

BACKGROUND

The discovery of cell free DNA has promoted the noninvasive detection of alterations in genomic sequences that occur in various disease states. However, in some instances, e.g., cancer, the ability to determine the presence of disease by detecting disease-associated mutations has been hindered by the extremely low levels of cell free tumor DNA. Methods that allow for the accurate detection of disease-associated mutations remain desirable. In addition, there also remains a need for the determination of tumor fraction in pre- and post-treatment cancer patients.

Similarly, inherited mutations that result in disease in a fetus remain difficult due to the low concentration of cell free fetal DNA in maternal blood. Prenatal genetic testing allows early detection of genetic disease in a fetus. Many fetal genetic disorders arise from large chromosomal defects, such as aneuploidy. Other disorders can be a result of inherited or de novo mutations, such as single nucleotide variants, multiple nucleotide variants, insertion or deletion variants ("indel" variants), or copy number variants. During pregnancy, many soon-to-be parents or physicians want to understand the risk of such disorders in an unborn fetus to prepare for any undesirable diagnosis. This is especially true when the parents are each carriers for the same disease. Thus, there remains a need for accurate detection of fetal disease-associated mutations in a non-invasive manner.

SUMMARY OF THE INVENTION

Provided herein, there is an assay comprising: identifying a plurality of probes useful in the detection of at least one segregating marker; selecting a unique combination of probes wherein the probes are designed to detect either (i) a marker of interest or (ii) a segregating sequence at a marker of interest, or a combination thereof; contacting said unique combination of probes to a nucleic acid sample; and determining the presence or absence of a segregating sequence at the marker of interest.

Also provided herein, there is an assay comprising: identifying a plurality of probes useful in the detection of an individual subject's nucleic acid in a test nucleic acid sample, said test sample comprising a mixture of nucleic acids from multiple sources; selecting a unique combination of probes wherein the probes are designed to detect either (i) a marker of interest, or a mutation in a marker of interest, or a combination thereof; contacting said unique combination of probes to a nucleic acid sample; and determining the presence or absence of a subject's nucleic acid in said test nucleic acid sample.

Additionally, provided herein is a personalized method for determining tumor fraction in a patient comprising: screening genomic DNA from tumor tissue from a patient to identify a set of somatic mutations; identifying a subset of somatic mutations specific to said patient's tumor from said set of mutations to create a signature panel of mutations, said panel being specific for said patient; and screening said signature panel to ascertain the proportion of circulating tumor DNA in said cell free DNA from said patient thereby determining the tumor fraction in said patient.

In some embodiments, the probes are calibrated to maximize detection of at least one segregating marker or of an individual subject's nucleic acid sequence. In some embodiments, the probes are calibrated to maximize detection of at least one segregating marker. In some embodiments, the probes are calibrated to maximize detection of an individual subject's nucleic acid sequence. In some embodiments, the probes are calibrated to maximize detection of at least one segregating marker or of an individual subject's nucleic acid sequence. In some embodiments, the probes are selected from a panel of prepared probes, wherein each probe is contained in a tube in tube rack in a bank of said prepared probes. In some embodiments, the plurality of probes is unique for each patient or sample.

In some embodiments, the nucleic acid is DNA. In some embodiments, the DNA is fragmented. In some embodiments, the DNA is cell-free DNA. In some embodiments, the nucleic acid is RNA. In some embodiments, each probe in the plurality of probes is selected from a bank of prepared probes with the aid of a tube picker.

In some embodiments, the identifying said first set of segregating markers and said subset of segregating markers comprises whole genome sequencing or targeted sequencing. In some embodiments, the targeted sequencing is to a subset of sites of the whole genome. In some embodiments, the targeted sequencing is to introns, exons, non-coding or a combination thereof. In some embodiments, the segregating marker is either an inherited mutation or a somatic mutation.

In some embodiments, the nucleic acid sample is derived from a biological sample. In some embodiments, the nucleic acid sample is derived from a tumor sample. In some embodiments, the nucleic acid sample is a mixture of nucleic acids derived from more than one source or individual. In some embodiments, the nucleic acid sample comprises fetal nucleic acids. In some embodiments, the nucleic acid sample comprises tumor nucleic acids. In some embodiments, the nucleic acid sample comprises a mixture of nucleic acids from two or more individuals.

In some embodiments, the determining comprises comparing the test nucleic acid to a reference nucleic acid. In some embodiments, the reference nucleic acid is a human genomic sequence. In some embodiments, the reference nucleic acid is either a maternal or paternal nucleic acid sequence. In some embodiments, the reference sequence is a matched non-tumor nucleic acid sequence.

In some embodiments, the assay is automated.

In some embodiments, screening is done on matched tumor and non-tumor tissue from a patient. In some embodiments, identifying said first set of mutations and said subset of mutations comprises whole genome sequencing or targeted sequencing. In some embodiments, the targeted sequencing is to introns, exons or a combination thereof. In some embodiments, the screening said signature panel comprises targeted sequencing of said set of somatic mutations. In some embodiments, the comprising re-screening said personalized panel of mutations at one or more times during treatment to determine the efficacy of said treatment. In some embodiments, the comprising re-screening said personalized panel of mutations at one or more times following completion of treatment to determine recurrence of cancer. In some embodiments, the said mutations in said signature panel of mutations comprise one or more mutations selected from SNPs, insertions, deletions, and translocations. In some embodiments, the said cell free DNA is obtained from a biological fluid. In some embodiments, the said cell free DNA is obtained from blood plasma. In some embodiments, the said cell free DNA is obtained from urine. In some embodiments, the said cell free DNA is obtained from saliva.

BRIEF DESCRIPTION OF THE DRAWINGS

FIG. 6 shows a table of the results obtained for detection of "cancer" sites in a background of 1,000,000 total sequences, i.e., "cancer" and normal sequences. Reference is made to Example 2.

DETAILED DESCRIPTION

Figure 1:
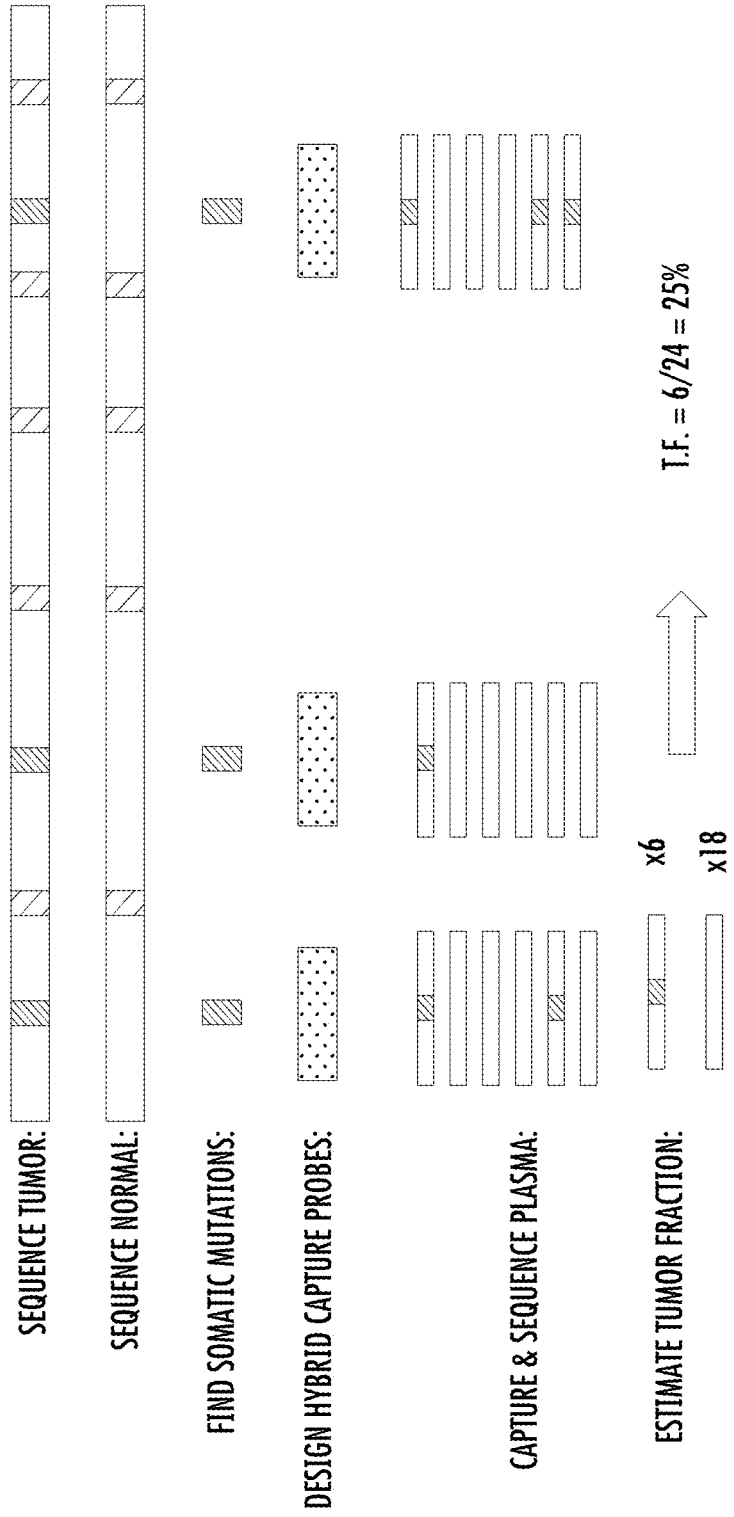
FIG. 1 illustrates the workflow for identifying a panel of somatic mutations in a patient, e.g., a cancer patient, and determining the tumor burden for the patient from targeted sequences in the patient's cell free DNA.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X". Additionally, use of "about" preceding any series of numbers includes "about" each of the recited numbers in that series. For example, description referring to "about X, Y, or Z" is intended to describe "about X, about Y, or about Z."

It is understood that aspects and variations of the invention described herein include "consisting" and/or "consisting essentially of" aspects and variations.

A "set" of reads refers to all sequencing reads with a common parent nucleic acid strand, which may or may not have had errors introduced during sequencing or amplification of the parent nucleic acid strand.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Definitions

The term "signature panel" herein refers to a collection of sequences comprising somatic mutations that is specific to a patient, or markers that distinguish between two or more individuals. A signature panel may distinguish one sample from another.

The term "tumor burden" herein refers to the total amount of tumor material present in a patient, which can be reflected by the tumor fraction as determined according to the method provided herein.

The term "tumor fraction" herein refers to the proportion of circulating cell free tumor DNA (ctDNA) relative to the total amount of cell free DNA (cfDNA). Tumor fraction is believed to be indicative of the size of the tumor.

The term "genomic DNA" or "DNA" herein refers to DNA of a cellular genome. The genomic DNA can be cellular, i.e., contained within a cell, or it can be cell free.

The term "sample" herein refers to any substance containing or presumed to contain nucleic acid. The sample can be a biological sample obtained from a subject. The nucleic acids can be RNA, DNA, e.g., genomic DNA, mitochondrial DNA, viral DNA, synthetic DNA, or cDNA reverse transcribed from RNA. The nucleic acids in a nucleic acid sample generally serve as templates for extension of a hybridized primer. In some embodiments, the biological sample is a biological fluid sample. The fluid sample can be whole blood, plasma, serum, ascites, cerebrospinal fluid, sweat, urine, tears, saliva, buccal sample, cavity rinse, or organ rinse. The fluid sample can be an essentially cell-free liquid sample (e.g., plasma, serum, sweat, urine, tears, etc). In other embodiments, the biological sample is a solid biological sample, e.g., feces or tissue biopsy, e.g., a tumor biopsy. A sample can also comprise in vitro cell culture constituents (including but not limited to conditioned medium resulting from the growth of cells in cell culture medium, recombinant cells and cell components). In some embodiments, the sample is a biological sample that is a mixture of nucleic acids from multiple sources, i.e., there is more than one contributor to a biological sample, e.g., two or more individuals.

The term "target sequence" herein refers to a selected target polynucleotide, e.g., a sequence present in a cfDNA molecule, whose presence, amount, and/or nucleotide sequence, or changes in these, are desired to be determined. Target sequences are interrogated for the presence or absence of a somatic mutation. The target polynucleotide can be a region of gene associated with a disease. In some embodiments, the region is an exon. The disease can be cancer.

The terms "anneal", "hybridize" or "bind," can refer to two polynucleotide sequences, segments or strands, and can be used interchangeably and have the usual meaning in the art. Two complementary sequences (e.g., DNA and/or RNA) can anneal or hybridize by forming hydrogen bonds with complementary bases to produce a double-stranded polynucleotide or a double-stranded region of a polynucleotide.

The term "marker" or "segregating marker" refers to a moiety that is used to discriminate between two or more samples, e.g., two or more individuals or tissues. A marker may be a nucleic acid (e.g., a gene), small molecule, peptide, fatty acid, metabolite, protein, lipid, etc. A marker may be a mutation. A marker may be a synthetic nucleic acid. A marker or set of markers may define a genetic signature of an entity, e.g., an individual, relative to a second nucleic acid, e.g., a reference nucleic acid sequence.

The term "mutation" herein refers to a change introduced into a reference sequence, including, but not limited to, substitutions, insertions, deletions (including truncations) relative to the reference sequence. Mutations can involve large sections of DNA (e.g., copy number variation). Mutations can involve whole chromosomes (e.g., aneuploidy). Mutations can involve small sections of DNA. Examples of mutations involving small sections of DNA include, e.g., point mutations or single nucleotide polymorphisms (SNPs), multiple nucleotide polymorphisms, insertions (e.g., insertion of one or more nucleotides at a locus but less than the entire locus), multiple nucleotide changes, deletions (e.g., deletion of one or more nucleotides at a locus), and inversions (e.g., reversal of a sequence of one or more nucleotides). The consequences of a mutation include, but are not limited to, the creation of a new character, property, function, phenotype or trait not found in the protein encoded by the reference sequence. In some embodiments, the reference sequence is a parental sequence. In some embodiments, the reference sequence is a reference human genome, e.g., h19. In some embodiments, the reference sequence is derived from a non-cancer (or non-tumor) sequence. In some embodiments, the mutation is inherited. In some embodiments, the mutation is spontaneous or de novo.

The terms "treat", "treatment" and "treating" refer to the reduction or amelioration of the progression, severity and/or duration of a proliferative disorder e.g., cancer, or the amelioration of a proliferative disorder resulting from the administration of one or more therapies.

The terms "cancer" and "tumor" are used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

As used herein, the term "barcode" (also termed single molecule identifier (SMI)) refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are about or at least about 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different lengths than barcodes associated with other polynucleotides. In general, barcodes are of sufficient length and include sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at at least three nucleotide positions, such as at least 3, 4, 5, 6, 7, 8, 9, 10, or more nucleotide positions. A plurality of barcodes may be represented in a pool of samples, each sample including polynucleotides comprising one or more barcodes that differ from the barcodes contained in the polynucleotides derived from the other samples in the pool. Samples of polynucleotides including one or more barcodes can be pooled based on the barcode sequences to which they are joined, such that all four of the nucleotide bases A, G, C, and T are approximately evenly represented at one or more positions along each barcode in the pool (such as at 1, 2, 3, 4, 5, 6, 7, 8, or more positions, or all positions of the barcode).

The term "base pair" or "bp" as used herein refers to a partnership (i.e., hydrogen bonded pairing) of adenine (A) with thymine (T), or of cytosine (C) with guanine (G) in a double stranded DNA molecule. In some embodiments, a base pair may include A paired with Uracil (U), for example, in a DNA/RNA duplex.

A "causal genetic variant" is a genetic variant for which there is statistical, biological, and/or functional evidence of association with a disease or trait.

The term "copy number variant" or "CNV" refers to any duplication or deletion of a genomic segment. A "copy number loss variant" or "CNLV" refers to a deletion of a genomic segment of more than about 100 base pairs.

The term "indel variant" refers to an insertion or a deletion variant.

The term "microdeletion" refers to a deletion of about 2 million base pairs to about 7 million base pairs.

The term "random or systematic error" means an artificially introduced sequence artifact.

The term "small nucleotide polymorphism" or "SNP" refers to a single-nucleotide variant (SNV), a multi-nucleotide variant (MNV), or an indel variant about 100 base pairs or less.

In general, a "complement" of a given nucleic acid sequence is a sequence that is fully complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g., thermodynamically more stable under a given set of conditions, such as stringent conditions commonly used in the art) in comparison with hybridization with non-target sequences during a hybridization reaction. Typically, hybridizable sequences share a degree of sequence complementarity over all or a portion of their respective lengths, such as 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "complementary" herein refers to the broad concept of sequence complementarity in duplex regions of a single polynucleotide strand or between two polynucleotide strands between pairs of nucleotides through base-pairing. It is known that an adenine nucleotide is capable of forming specific hydrogen bonds ("base pairing") with a nucleotide, which is thymine or uracil. Similarly, it is known that a cytosine nucleotide is capable of base pairing with a guanine nucleotide. However, in certain circumstances, hydrogen bonds may also form between other pairs of bases, e.g., between adenine and cytosine, etc. "Essentially complementary" herein refers to sequence complementarity in duplex regions of a single polynucleotide strand or between two polynucleotide strands, for example, wherein the complementarity is less than 100% but is greater than 90%, and retains the stability of the duplex region.

The term "derived from" encompasses the terms "originated from," "obtained from," "obtainable from," "isolated from," and "created from," and generally indicates that one specified material finds its origin in another specified material or has features that can be described with reference to the another specified material.

A "gene" refers to a DNA segment that is involved in producing a polypeptide and includes regions preceding and following the coding regions as well as intervening sequences (introns) between individual coding segments (exons).

"Hybridization" and "annealing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may include two nucleic acid strands forming a duplex structure, three or more strands forming a multi-stranded complex, a single self-hybridizing strand, or any combination of these. A hybridization reaction may constitute a step in a more extensive process, such as the initiation of polymerase chain reaction (PCR), ligation reaction, sequencing reaction, or cleavage reaction, e.g., enzymatic cleavage of a polynucleotide by a ribozyme. A first nucleic acid sequence that can be stabilized via hydrogen bonding with the bases of the nucleotide residues of a second sequence is said to be "hybridizable" to the second sequence. In such a case, the second sequence can also be said to be hybridizable to the first sequence. The term "hybridized" refers to a polynucleotide in a complex that is stabilized via hydrogen bonding between the bases of the nucleotide residues.

The term "library" herein refers to a collection or plurality of template molecules, i.e., target DNA duplexes, which share common sequences at their 5' ends and common sequences at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates must be related in terms of sequence and/or source.

The term "Next Generation Sequencing (NGS)" herein refers to sequencing methods that allow for massively parallel sequencing of clonally amplified and of single nucleic acid molecules during which a plurality, e.g., millions, of nucleic acid fragments from a single sample or from multiple different samples are sequenced in unison. Non-limiting examples of NGS include sequencing-by-synthesis, sequencing-by-ligation, real-time sequencing, and nanopore sequencing.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of polymeric operatively linked nucleotides is typically referred to herein as a "base sequence" or "nucleotide sequence," or nucleic acid or polynucleotide "strand," and is represented herein by a formula whose left to right orientation is in the conventional direction of 5'-terminus to 3'-terminus, referring to the terminal 5' phosphate group and the terminal 3' hydroxyl group at the "5" and "3" ends of the polymeric sequence, respectively.

The term "nucleotide analog" herein refers to analogs of nucleoside triphosphates, e.g., (S)-Glycerol nucleoside triphosphates (gNTPs) of the common nucleobases: adenine, cytosine, guanine, uracil, and thymidine (Horhota et al., Organic Letters, 8:5345-5347 [2006]). Also encompassed are nucleoside tetraphosphate, nucleoside pentaphosphates and nucleoside hexaphosphates.

The term "operably linked" refers to a juxtaposition or arrangement of specified elements that allows them to perform in concert to bring about an effect. For example, a promoter is operably linked to a coding sequence if it controls the transcription of the coding sequence.

The term "polymerase" herein refers to an enzyme that catalyzes the polymerization of nucleotides (i.e., the polymerase activity). The term polymerase encompasses DNA polymerases, RNA polymerases, and reverse transcriptases. A "DNA polymerase" catalyzes the polymerization of deoxyribonucleotides. An "RNA polymerase" catalyzes the polymerization of ribonucleotides. A "reverse transcriptase" catalyzes the polymerization of deoxyribonucleotides that are complementary to an RNA template.

The terms "polynucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown, and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)ORT, CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need and circular portions. The following are nonlimiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may include modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component, tag, reactive moiety, or binding partner. Polynucleotide sequences, when provided, are listed in the 5' to 3' direction, unless stated otherwise.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may include modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "primer" herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and a polymerase enzyme, e.g., a thermostable enzyme, in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the polymerase, e.g., thermostable polymerase enzyme. The exact lengths of a primer will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "sequencing library" herein refers to DNA that is processed for sequencing, e.g., using massively parallel methods, e.g., NGS. The DNA may optionally be amplified to obtain a population of multiple copies of processed DNA, which can be sequenced by NGS.

The term "single stranded overhang" or "overhang" is used herein to refer to a strand of a double stranded (ds) nucleic acid molecule that extends beyond the terminus of the complementary strand of the ds nucleic acid molecule. The term "5' overhang" or "5' overhanging sequence" is used herein to refer to a strand of a ds nucleic acid molecule that extends in a 5' direction beyond the 3' terminus of the complementary strand of the ds nucleic acid molecule. The term "3' overhang" or "3' overhanging sequence" is used herein to refer to a strand of a ds nucleic acid molecule that extends in a 3' direction beyond the 5' terminus of the complementary strand of the ds nucleic acid molecule.

A "spacer" may consist of a repeated single nucleotide (e.g., 1, 2, 3, 4, 5, 6, 7, 8, 9, 10, or more of the same nucleotide in a row), or a sequence of 2, 3, 4, 5, 6, 7, 8, 9, 10, or more nucleotides repeated 1, 2, 3, 4, 5, 6, 7, 8, 9, 10, or more times. A spacer may comprise or consist of a specific sequence, such as a sequence that does not hybridize to any target sequence in a sample. A spacer may comprise or consist of a sequence of randomly selected nucleotides.

The phrases "substantially similar" and "substantially identical" in the context of at least two nucleic acids typically means that a polynucleotide includes a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical nucleic acid molecules hybridize to each other under stringent conditions (e.g., within a range of medium to high stringency).

Nucleic acid "synthesis" herein refers to any in vitro method for making a new strand of polynucleotide or elongating an existing polynucleotide (i.e., DNA or RNA) in a template dependent manner. Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

The term "tag" refers to a detectable moiety that may be one or more atom(s) or molecule(s), or a collection of atoms and molecules. A tag may provide an optical, electrochemical, magnetic, or electrostatic (e.g., inductive, capacitive) signature.

The term "tagged nucleotide" herein refers to a nucleotide that includes a tag (or tag species) that is coupled to any location of the nucleotide including, but not limited to a phosphate (e.g., terminal phosphate), sugar or nitrogenous base moiety of the nucleotide. Tags may be one or more atom(s) or molecule(s), or a collection of atoms and molecules. A tag may provide an optical, electrochemical, magnetic, or electrostatic (e.g., inductive, capacitive) signature.

The term "target DNA duplex" herein refers to a double stranded DNA molecule that is derived from a sample polynucleotide that is DNA, e.g., genomic or cell-free DNA ("cfDNA"), and/or RNA.

As used herein, the term "target polynucleotide" refers to a nucleic acid molecule or polynucleotide in a population of nucleic acid molecules having a target sequence to which one or more oligonucleotides are designed to hybridize. In some embodiments, a target sequence uniquely identifies a sequence derived from a sample, such as a particular genomic, mitochondrial, bacterial, viral, or RNA (e.g., mRNA, miRNA, primary miRNA, or pre-miRNA) sequence. In some embodiments, a target sequence is a common sequence shared by multiple different target polynucleotides, such as a common adapter sequence joined to different target polynucleotides. "Target polynucleotide" may be used to refer to a double-stranded nucleic acid molecule that includes a target sequence on one or both strands, or a single-stranded nucleic acid molecule including a target sequence, and may be derived from any source of or process for isolating or generating nucleic acid molecules. A target polynucleotide may include one or more (e.g., 1, 2, 3, 4, 5, 6, 7, 8, 9, 10, or more) target sequences, which may be the same or different. In general, different target polynucleotides include different sequences, such as one or more different nucleotides or one or more different target sequences.

The term "template DNA molecule" herein refers to a strand of a nucleic acid from which a complementary nucleic acid strand is synthesized by a DNA polymerase, for example, in a primer extension reaction.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene*, 4th Ed., W. A. Benjamin, Inc., Menlo Park, Calif. (1987)).

A "sample" may include, but is not limited to, blood, plasma, saliva, urine, semen, amniotic fluid, oocytes, skin, hair, feces, cheek swabs, or pap smear lysate from an individual.

A "tube rack" refers to a tube holder with a plurality of slots for holding sample tubes. The tube rack is typically configured to hold sample tubes in an upright manner.

"Coded information" or "identification code" refers to information that can be retrieved to identify a sample, the source of a sample, and/or information about a sample (e.g., a patient from whom a sample was obtained, a tissue source, etc.). Coded information may, for example, be in the form of a one-dimensional, two-dimensional, or three-dimensional barcode.

A "portion adjacent to a region of interest" refers to a sequence that is immediately proximal to a region of interest. Reference to a "portion of or adjacent to a region of interest" refers to a sequence that 1) is entirely within the region of interest, 2) is entirely outside but immediately proximal to the region of interest, or 3) includes a contiguous sequence from within and immediately proximal to the region of interest. Reference to a "sequence that is substantially complementary to a portion of or adjacent to a region of interest" refers to 1) a sequence that is substantially complementary to a sequence entirely within the region of interest, 2) a sequence substantially complementary to a sequence entirely outside but immediately proximal to the region of interest, or 3) a sequence that is substantially complementary to a contiguous sequence from with and immediately proximal to the region of interest.

The term "average" as used herein refers to either a mean or a median, or any value used to approximate the mean or the median, unless the context clearly indicates otherwise.

It is understood that aspects and variations of the invention described herein include "consisting" and/or "consisting essentially of" aspects and variations.

The term "substantially complementary" is used to refer to two nucleic acid sequences (X and Y) on opposite strands for which both are at least 12 bases in length and the complementarity fraction between them is at least 0.75. The complementarity fraction is calculated as follows. First, the optimal alignment between X and the reverse complement of Y is calculated with the Needleman-Wunsch algorithm (Needleman et al., *A general method applicable to the search for similarities in the amino acid sequence of two proteins*. Journal of Molecular Biology, vol. 48 (3), pp. 443-453(1970)) using default parameters (i.e., match=+1, mismatch=−1, and gap=−1). Then, the number of matches is counted for the optimal alignment. Finally, the complementarity fraction is defined as the number of matches divided by the smaller of the lengths of either sequence, i.e., the fraction of the length that is complementary. The term "substantially complementary" includes completely complementary nucleic acid strands.

A "tile" refers to one or more contiguous loci within a region of interest. A region of interest can be divided into one or more tiles. The tiles can be, but need not be, contiguous. Therefore, the region of interest can optionally include non-contiguous sub-regions. The tiles can be of the same length or of different lengths. A "locus" refers to one or more contiguous bases, and is fully contained within the tile.

DNA Library Preparation (with Optional Sequence Tag or Molecular Barcode Integration)

In some embodiments of the methods disclosed herein, a DNA library is obtained or prepared from cell-free DNA obtained from a patient, e.g., a pregnant woman. In some embodiments, a maternal DNA library is obtained or prepared from the maternal genome of the pregnant woman. In some embodiments, a paternal DNA library is obtained or prepared from a paternal genome. In some embodiments, the maternal and/or the paternal DNA has been previously sequenced and mutations identified. The DNA library comprises a population of DNA molecules. The DNA molecules are generally of sufficient length such that they can be accurately analyzed by sequencing or digital PCR. See, e.g., U.S. Pat. App. Nos. 2013/0225452 and 2012/0208705.

When producing a DNA library from genomic DNA, the genomic DNA can be fragmented, for example by suing a hydrodynamic shear or other mechanical force, or fragmented by chemical or enzymatic digestion, such as restriction digesting. This fragmentation process allows the DNA molecules present in the genome to be sufficiently short for analysis, such as sequencing or digital PCR. Cell-free DNA, however, is generally sufficiently short such that no fragmentation is necessary. Cell-free DNA originates from genomic DNA. A portion of the cell-free DNA obtained from a plasma sample of a pregnant mother originates from the maternal genome and a portion of the cell-free DNA originates form the fetal genome.

In some embodiments, the DNA molecules are subjected to additional modification, resulting in the attachment of oligonucleotides to the DNA molecules. The oligonucleotides can comprise an adapter sequence or a molecular barcode (or both). In some embodiments, the adapter sequence is common to all oligonucleotides in a plurality of oligonucleotides that are used to form the DNA library. In some embodiments, the molecular barcodes are unique or have low redundancy. By way of example, the oligonucleotide can be attached to the DNA molecules by ligation. Direct attachment of the oligonucleotides to the DNA molecules in the DNA library can be used, for example, when enrichment occurs in a downstream process. For example, in some embodiments, a DNA library is prepared by direct attachment of an oligonucleotide comprising a molecular barcode and an adapter sequence, followed by enrichment (for example, by hybridization) of DNA molecules comprising a region of interest or a portion of a region of interest.

In some embodiments, library preparation and enrichment occurs simultaneously. For example, in some embodiments, DNA molecules comprising a region of interest or a portion thereof are preferentially amplified. This can be done, for example, by combining the cell-free DNA (or genomic DNA), with oligonucleotides comprising a target-specific sequence, an adapter sequence, and a molecular barcode, and amplifying the DNA molecules. As before, in some embodiments, the adapter sequence is common to all oligonucleotides in a plurality of oligonucleotides, and the molecular barcode is unique or of low redundancy. The target-specific sequence is unique to the targeted region of interest or portion thereof. Thus, PCR amplification selectively amplifies the DNA molecules comprising the region of interest or portion thereof.

When the methods include the use of tags or molecular barcodes, the tag or molecular barcode may also be ligated to the fragments or included within the ligated adapter sequences. The independent attachment of the tag or molecular barcode, as opposed to incorporating the tag or molecular barcode, may vary with the enrichment method. For example, when using hybrid capture-based target enrichment the adapter can include the molecular barcode, when using PCR-targeted enrichment target-specific primer pairs and overhangs are used that will incorporate the sequencing adapters and sample-specific and molecular barcodes, and when using on-sequencer enrichment the adapter may be separately ligated from the tag or molecular barcode.

Targeted Enrichment of a Region of Interest (or Portion Thereof)

The disclosure contemplates methods for enriching a target sequence in a region of interest. Enrichment techniques are known in the art. See, e.g., WO2013/112923; Mertes et al., *Targeted enrichment of genomic DNA regions for next-generation sequencing*, Briefings in Functional Genomics, vol. 10(6), pp. 374-386 (2011). Exemplary enrichment techniques include, but are not limited to, hybrid capture, selective circularization (also referred to as molecular inversion probes (MIP)), and PCR amplification of targeted regions of interest. Hybrid capture methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g., biotin) which can subsequently be immobilized to a solid surface, such as a bead (in-solution capture). Molecular inversion probe (MIP)-based method relies on construction of numerous single-stranded linear oligonucleotide probes, consisting of a common linker flanked by target-specific sequences. Upon annealing to a target sequence, the probe gap region is filled via polymerization and ligation, resulting in a circularized probe. The circularized probes are then released and amplified using primers directed at the common linker region. PCR-based methods employ highly parallel PCR amplification, where each target sequence in the sample has a corresponding pair of unique, sequence-specific primers. In some embodiments, enrichment of a target sequence occurs at the time of sequencing.

Sequencing

The disclosure contemplates methods of sequencing the sequence library. Sequencing may be by any method known in the art. Sequencing methods include, but are not limited to, Maxam-Gilbert sequencing-based techniques, chain-termination-based techniques, shotgun sequencing, bridge PCR sequencing, single-molecule real-time sequencing, ion semiconductor sequencing (Ion Torrent sequencing), nanopore sequencing, pyrosequencing (454), sequencing by synthesis, sequencing by ligation (SOLiD sequencing), sequencing by electron microscopy, dideoxy sequencing reactions (Sanger method), massively parallel sequencing, polony sequencing, and DNA nanoball sequencing. In some embodiments, sequencing involves hybridizing a primer to the template to form a template/primer duplex, contacting the duplex with a polymerase enzyme in the presence of a detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotide determines the sequence of the nucleic acid. In some embodiments, the sequencing comprises obtaining paired end reads. The accuracy or average accuracy of the sequence information may be greater than 80%, 90%, 95%, 99% or 99.98%. In some embodiments, the sequence information obtained is more than 50 bp, 100 bp or 200 bp. The sequence information may be obtained in less than 1 month, 2 weeks, 1 week 1 day, 3 hours, 1 hour, 30 minutes, 10 minutes, or 5 minutes. The sequence accuracy or average accuracy may be greater than 95% or 99%. The sequence coverage may be greater than 20 fold or less than 500 fold. Exemplary detectable labels include radiolabels, florescent labels, enzymatic labels, etc. In some embodiments, the detectable label may be an optically detectable label, such as a fluorescent label. Exemplary fluorescent labels include cyanine, rhodamine, fluorescien, coumarin, BODIPY, alexa, or conjugated multi-dyes. In some embodiments, the nucleotide is flagged if one or more of its sequence segments are substantially similar to one or more sequence segments of another nucleotide within the same partition.

It is also contemplated that some methods of sequencing the sequence library do not involve a prior target enrichment step. For example, use of on-sequencer enrichment, such as with a nanopore sequencer, allows for the "simultaneous" enrichment and sequencing of the sequence library by real-time rejection of molecules that are not from the region of interest. Alternatively, sequences can be selectively and preferentially sequenced from the region of interest.

In some embodiments, the method utilizes a duplex sequencing method. This method is described, for example, in co-pending U.S. Provisional Application 62/452,848, filed 31 Jan. 2017, entitled "Methods and Compositions for Enrichment of Target Polynucleotides" and may utilize molecular barcodes as described herein below.

Molecular Barcodes

In some embodiments, an identifier sequence, i.e., a molecular barcode is used to identify unique DNA molecules in a DNA library. See, e.g., U.S. Pat. App. Nos. 2013/0261019 and 2015/0080266. See also co-pending U.S. Provisional Applications 62/348,791 filed 10 Jun. 2016, 62/364,256 filed 19 Jul. 2016, and 62/447,784 filed 18 Jan. 2017, all entitled Nucleic Acid Adapters and Uses Thereof. The molecular barcodes aid in reconstruction of a contiguous DNA sequences or assist in copy number variation determination. Exemplary markers include nucleic acid binding proteins, optical labels, nucleotide analogs, nucleic acid sequences, and others known in the art.

In some embodiments, the molecular barcode is a nanostructure barcode. In some embodiments, the molecular barcode comprises a nucleic acid sequence that when joined to a target polynucleotide serves as an identifier of the sample or sequence from which the target polynucleotide was derived. In some embodiments, molecular barcodes are at least 3, 4, 5, 6, 7, 8, 9, 10, 11, 12, 13, 14, 15, or more nucleotides in length. In some embodiments, molecular barcodes are shorter than 10, 9, 8, 7, 6, 5, or 4 nucleotides in length. In some embodiments, each molecular barcode in a plurality of molecular barcodes differ from every other molecular barcode in the plurality at least three nucleotide positions, such as at least 3, 4, 5, 6, 7, 8, 9, 10, or more positions. In some embodiments, molecular barcodes associated with some polynucleotides are of different length than molecular barcodes associated with other polynucleotides. In general, molecular barcodes are of sufficient length and comprise sequences that are sufficiently different to allow the identification of samples based on molecular barcodes with which they are associated. In some embodiments, both the forward and reverse adapter comprise at least one of a plurality of molecular barcode sequences. In some embodiments, each reverse adapter comprises at least one of a plurality of molecular barcode sequences, wherein each molecular barcode sequence of the plurality of molecular barcode sequences differs from every other molecular barcode sequence in the plurality of molecular barcode sequences.

Various sets of molecular barcodes have been reported in the literature. Several researchers have used sets that satisfy the conditions imposed by a Hamming Code (Hamady et al., *Error-correcting barcoded primers allow hundreds of samples to by pyrosequenced in multiplex*, Nature Methods, vol. 5(3), pp. 235-237 (2008); and Lefrançois et al., *Efficient yeast ChiP-Seq using multiplex short-read DNA sequencing*, BMC Genomics, vol. 10, pp. 1-18 (2009). Others have used sets that satisfy more complex conditions than a Hamming Code but share the similar guarantee of a certain minimal pairwise Hamming distance (Fierer et al., *The influence of sex, handedness, and washing on the diversity of hand surface bacteria*, Proc. Nat'l Adad. Sci., vol. 105, pp. 17,994-17,999 (2008); Krishnan et al., *Barcodes for DNA sequencing with guaranteed error correction and capability*, Electronics Letters, vol. 47, pp. 236-237 (2011). As an alternative to Hamming-distance based molecular barcodes, others have selected sets of molecular barcodes which satisfy a minimum pairwise edit distance. Sets of such molecular barcodes can work with insertion, deletion or substitution errors in the read of a barcode sequence.

In some embodiments, every molecular barcode in a set is unique, that is, any two molecular barcodes chosen out of a given set will differ in at least one nucleotide position. Furthermore, it is contemplated that molecular barcodes have certain biochemical properties that are selected based on how the set will be used. For example, certain sets of molecular barcodes that are used in an RT-PCR reaction should not have complementary sequences to any sequence in the genome of a certain organism or set of organisms. A requirement for non-complementarity helps to ensure that the use of a particular molecular barcode sequence will not result in mis-priming during molecular biological manipulations requiring primers, such as reverse transcription or PCR. Certain sets satisfy other biochemical properties imposed by the requirements associated with the processing of the sequence molecules into which the barcodes are incorporated.

Examples of sequencing technologies for sequencing molecular barcodes, as well as any generated nucleotide-based sequence, include, but are not limited to, Maxam-Gilbert sequencing-based techniques, chain-termination-based techniques, shotgun sequencing, bridge PCR sequencing, single-molecule real-time sequencing, ion semiconductor sequencing (Ion Torrent sequencing), nanopore sequencing, pyrosequencing (454), sequencing by synthesis, sequencing by ligation (SOLiD sequencing), sequencing by electron microscopy, dideoxy sequencing reactions (Sanger method), massively parallel sequencing, polony sequencing, and DNA nanoball sequencing.

In some embodiments, molecular barcodes are used to improve the power of copy-number calling algorithms by reducing non-independence from PCR duplication. In another embodiment, molecular barcodes can be used to improve test specificity by reducing sequence error generated during amplification.

Disease Testing

Aspects of the invention relate to methods that improve the detection, monitoring and treatment of a patient suffering from a disease. The disease can be a cancer. The patient can be suspected or known to harbor a solid tumor, or can be a subject who previously harbored a solid tumor. In some aspects the solid tumor is a tumor of a tissue or organ. In other aspects, the solid tumor is a metastatic mass of a blood borne cancer. The present method can also be applicable to the detection and/or monitoring of blood borne cancers.

Genotyping tumor tissue in search of somatic genetic alterations for actionable information has become routine practice in clinical oncology. However, tumor tissue is a single snapshot in time, is subject to selection bias resulting from tumor heterogeneity, and can be difficult to obtain. Additionally, in cases when the tumor is removed, tumor tissue can only become available once the tumor has returned and has advanced sufficiently to be detected as a mass. Cell-free fragments of DNA are shed into the bloodstream by cells undergoing apoptosis or necrosis, and the load of circulating cell-free DNA (cfDNA) correlates with tumor staging and prognosis. The ability to detect and quantify tumor mutations in cfDNA has proven effective in tracking tumor dynamics in real time as well as serving as a liquid biopsy that can be used for a variety of clinical and investigational applications not previously possible. However, current methods are limited by the amount of blood that can be drawn for analysis, and by the extremely low proportions of tumor cfDNA of about 1e−4. The method provided herein combines analysis of patient-specific multiple somatic sites, e.g., single nucleotide polymorphisms (SNPs), which allows the detection of somatic mutations associated with the patient's cancer at extremely low proportions of tumor cfDNA of less than about 1e−3.

In one aspect, a method is provided for determining the tumor fraction from a biological sample from a patient suffering from a disease, e.g., cancer. The overview of the workflow of the method is provided in FIG. 1. The method can be represented by two phases. In a first phase, or enrollment phase, somatic mutations that are specific to a patient are identified, and a signature panel of capture probes, that are representative of the identified somatic mutations, is created. In a second phase, monitoring of the status of the cancer in the patient is performed using the patient's panel of capture probes to identify somatic mutations that are circulating as cell free DNA. The second phase is non-invasive and requires clinically viable amounts of a biological fluid, e.g., a peripheral blood draw of 10-20 ml, which can be repeated as frequently as desired to detect changes in the patient's cancer. A clinically viable amount of biological fluid, e.g., whole blood, typically comprises at least 1000 genome equivalents, at least 2000 genome equivalents, at least 3000 genome equivalents, at least 4000 genome equivalents, at least 5000 genome equivalents, at least 6000 genome equivalents, at least 7000 genome equivalents, at least 8000 genome equivalents, at least 9000 genome equivalents, at least 10000 genome equivalents, at least 11000 genome equivalents, at least 12000 genome equivalents, or at least 15000 genome equivalents. In some embodiments, the second phase of the method utilizes a whole blood sample of between 5 ml and 20 ml, comprising between 3000 and 15000 genome equivalents.

First, a panel of sequences comprising somatic mutations specific to the tumor of a patient is identified as follows. Genomic DNA is isolated from the tumor and from normal tissue, i.e., non-cancerous tissue, using any methods known in the art, and sequenced. DNA sequences form the tumor and non-tumor samples are compared, and a set of somatic mutations specific to the patient's tumor are identified. The set of the identified somatic mutations serves as a signature panel for the patient that can be sequenced at various stages of the disease, i.e., the signature panel can be screened to determine the presence of cancer at surgery following diagnosis; during cancer treatment, e.g., at intervals during chemotherapy or radiation therapy, to monitor the efficacy of the treatment; at intervals during remission to confirm continued absence of disease; and/or to detect recurrence of the disease.

Next, a set of capture probes is obtained. The set of capture probes comprises sequences that are capable of hybridizing to specific target sequences in the patient's genome and that encompass the sites comprising the tumor specific somatic mutations identified in the tumor tissue. In some embodiments, the set of capture probes are calibrated as in co-pending U.S. Provisional Application No. 62/447, 816, entitled "Balanced Capture Probes and Methods of Use Thereof".

Subsequently, the tumor fraction in a fluid sample from the same patient is determined. Determining the tumor fraction comprises obtaining cfDNA from the patient, and using the capture probes designed for the patient-specific signature panel of markers, e.g., mutations, capturing cfDNA target sequences comprising tumor and corresponding normal sequences. The captured sequences are analyzed and enumerated, and the tumor fraction is determined as the proportion of sequences comprising a somatic mutation of the total number of mutated and corresponding unmutated allelic sequences. Enumeration of mutated and unmutated allelic sequences is accomplished by analyzing the countable sequence reads obtained from the sequencing process. The method does not necessitate that all somatic mutations in the patient's signature panel be detected.

Pre-Natal Testing

Methods described herein are also useful in pre-natal testing, the parental, e.g., maternal and/or paternal, genotypes are known. The methods described herein are also useful in pre-natal testing, e.g., for analyzing numerous nucleic acids contained in a tissue sample (preferably serum or, more preferably, plasma) containing a mixture of nucleic acids from both the mother and the fetus.

In an aspect, the methods are used to determine if a fetus has inherited a deleterious combination of markers, e.g., mutations, from each parent putting the fetus at risk for disease, e.g., Lesch-Nyhan syndrome. The disease may be an autosomal recessive disease, e.g., Spinal Muscular Atrophy. The disease may be X-linked, e.g., Fragile X syndrome. The disease may be a disease caused by a dominant mutation in a gene, e.g., Huntington's Disease.

In some embodiments, the maternal nucleic acid sequence is the reference sequence. In some embodiments, the paternal nucleic acid sequence is the reference sequence. In some embodiments, the marker(s), e.g., mutation(s), are common to each parent. In some embodiments, the marker(s), e.g., mutation(s), are specific to one parent.

Haplotype Phasing

In some embodiments, haplotypes of an individual, such as maternal haplotypes, paternal haplotypes, or fetal haplotypes are constructed. The haplotypes comprise alleles co-located on the same chromosome of the individual. The process is also known as "haplotype phasing" or "phasing". A haplotype may be any combination of one or more closely linked alleles inherited as a unit. The haplotypes may comprise different combinations of genetic variants. Artifacts as small as a single nucleotide polymorphism pair can delineate a distinct haplotype. Alternatively, the results from several loci could be referred to as a haplotype. For example, a haplotype can be a set of SNPs on a single chromatid that is statistically associated to be likely to be inherited as a unit.

Methods or assays used to determine haplotype involve determining a contiguous nucleic acid sequence of a given length. Contiguous sequences may be derived from an individual sequence read, including either short or long read-length sequencing. Long read-length sequencing technologies include, for example, single molecule sequencing, such as SMRT Sequencing and nanopore sequencing technologies. See, e.g., Koren et al., *One chromosome, one contig: Complete microbial genomes from long-read sequencing and assembly*, Curr. Opin. Microbiol., vol. 23, pp. 110-120 (2014); and Branton et al., *The potential and challenges of nanopore sequencing*, Nat. Biotechnol., vol. 26, pp. 1146-1153 (2008). Contiguous sequences may also be derived from assembly of sequence reads that are aligned and assembled based upon overlapping sequences within the reads. When using multiple sequence reads, haplotype phasing can be determine by physically partitioning the originating molecular structures or by using other known linkage data, e.g., the tagging with molecular barcodes as described elsewhere herein. These overlapping sequence reads may likewise include short reads, e.g., less than 500 bases, such as, in some cases from approximately 100 to 500 bases, and in some cases from 100 to 250 bases, or based upon longer sequence reads, e.g., greater than 500 bases, 1000 bases or even greater than 10,000 bases. The short reads are phased by using, for example, 10× or Illumina synthetic long read molecular phasing technology, trio (e.g., mother, father, and offspring) or other relatives' genomic information, or statistical haplotype information. In some embodiments, the haplotypes are constructed using statistical mapping. See, e.g., U.S. Pat. App. No. 2015/0376700, hereby incorporated by reference; and Browning et al., *Haplotype phasing: Exisiting methods and new developments*, Nat. Rev. Genet., vol. 12, pp. 703-714 (2012).

In some embodiments, the maternal haplotype is used to distinguish between a fetal genetic variant and a maternal genetic variant, or to determine which of the two maternal chromosomal loci was inherited by the fetus.

X-linked Recessive Variant Detection

In some embodiments, provided herein is a method of detecting the presence or absence of a genetic variant in a region of interest in the genome of a fetus in a pregnant woman, wherein the fetal genetic variant is an X-linked recessive genetic variant. X-linked recessive disorders arise more frequently in male fetus because males with the disorder are hemizygous for the particular genetic variant. Example X-linked recessive disorders that can be detected using the methods described herein include Duchenne muscular dystrophy, Becker's muscular dystrophy, X-linked agammaglobulinemia, hemophilia A, and hemophilia B. These X-linked recessive variants can be inherited variants or de novo variants.

The methods described herein can be performed with or without constructing a maternal haplotype. Employing maternal haplotypes generally provides greater resolution of the fetal genetic variants, although substantial and accurate fetal genetic variant information can be resolved without constructing the maternal haplotype. In some embodiments, performing the method without maternal haplotypes allows for the accurate detection of large copy number variants (such as aneuploidy), microdeletions, paternally inherited X-linked recessive genetic variants, and de novo X-linked recessive genetic variants. In some embodiments, performing the method with maternal haplotypes allows for the accurate detection of large copy number variants (such as aneuploidy), microdeletions, paternally inherited X-linked recessive genetic variants, de novo X-linked recessive genetic variants, and maternally inherited X-linked genetic variants.

Cell-free DNA can be extracted from plasma of a pregnant woman (i.e., maternal plasma). The plasma comprises cell-free DNA from the fetal genome and cell-free DNA from the maternal genome. A DNA library is then formed from the cell-free DNA and the region of interest is enriched, thereby forming a population of enriched DNA molecules that correspond to the region of interest. The enriched DNA molecules are then sequenced to produce a plurality of cell-free sequencing reads. In some embodiments, molecular barcodes are employed. In some embodiments, the molecular barcodes are used to distinguish single nucleotide polymorphisms variants from random mutations. In some embodiments, the molecular barcodes are used to filter our redundantly counted DNA sequences.

The plurality of cell-free sequencing reads comprises sequencing reads from the fetal region of interest and sequencing reads from the maternal region of interest. An increase or decrease in the read frequency at a particular allele is computed, which indicates variance between the fetal genome and the maternal genome. A variant call can be made on the basis of that variance. In some embodiments, the variance is above (in the case of an increase in read frequency) or below (in the case of a decrease in read frequency) a predetermined threshold to trigger a variant call. Variance between the fetal and maternal genome for an X-linked region of interest is generally due to either a paternally inherited chromosome or a de novo mutation.

In addition to the accurate detection of large copy number variants (such as aneuploidy), microdeletions, paternally inherited X-linked recessive genetic variants, and de novo X-linked recessive genetic variants, maternally inherited X-linked variants in the fetus can be detected in methods using a maternal haplotype. In some embodiments, maternal genomic DNA is isolated from the pregnant mother, for example from leukocytes present in a buffy coat. At least one region of interest corresponding to the region of interest in the cell-free DNA is sequenced from the maternal genomic DNA. Optionally, the maternal genomic DNA is enriched at the corresponding region of interest. Also optionally, molecular barcodes are used with the maternal genomic DNA. The maternal haplotypes are then constructed, for example using molecular phasing technologies, using a sequence of a biological relative, or using statistical haplotype mapping.

An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome.

SNP Genetic Variant Detection

In some embodiments, provided herein is a method of detecting the presence or absence of a genetic variant in a region of interest in the genome of a fetus in a pregnant woman, wherein the fetal genetic variant is a de novo SNP genetic variant or a paternally-inherited SNP genetic variant. In some embodiments, the father's genome is sequenced to reveal whether the genetic variant is a paternally inherited genetic variant or a de novo genetic variant. That is, if the fetal genetic variant is not present in the father, and the described method indicates that the fetal genetic variant is distinguishable from the maternal genome, then the fetal genetic variant is a de novo variant. Accordingly, provided herein is a method of determining whether a fetal genetic variant is an inherited genetic variant or a de novo genetic variant.

Cell-free DNA can be extracted from plasma of a pregnant woman (i.e., maternal plasma). The plasma comprises cell-free DNA from the fetal genome and cell-free DNA from the maternal genome. A DNA library is then formed from the cell-free DNA and the region of interest is enriched, thereby forming a population of enriched DNA molecules that correspond to the region of interest. The enriched DNA molecules are then sequenced to produce a plurality of cell-free sequencing reads. In some embodiments, molecular barcodes are employed. In some embodiments, the molecular barcodes are used to distinguish single nucleotide polymorphisms variants from random mutations.

The plurality of cell-free sequencing reads comprises sequencing reads from the fetal region of interest and sequencing reads from the maternal region of interest. An increase or decrease in the read frequency at a particular allele is computed, which indicates variance between the fetal genome and the maternal genome. A variant call can be made on the basis of that variance. In some embodiments, the variance is above (in the case of an increase in read frequency) or below (in the case of a decrease in read frequency) a predetermined threshold to trigger a variant call. Variance between the fetal and maternal genome for a region of interest is generally due to either a paternally inherited chromosome or a de novo mutation.

In addition to the accurate detection of large copy number variants (such as aneuploidy), microdeletions, paternally inherited or de novo genetic variants, maternally inherited genetic variants in the fetus can be detected in methods using a maternal haplotype. In some embodiments, maternal genomic DNA is isolated from the pregnant mother, for example from leukocytes present in a buffy coat. At least one region of interest corresponding to the region of interest in the cell-free DNA is sequenced from the maternal genomic DNA. Optionally, the maternal genomic DNA is enriched at the corresponding region of interest. Also optionally, molecular barcodes are used with the maternal genomic DNA. The maternal haplotypes are then constructed, for example using molecular phasing technologies, using a sequence of a biological relative, or using statistical haplotype mapping.

An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome and is a fetal genetic variant.

To determine whether a fetal genetic variant is a de novo genetic variant or a paternally inherited genetic variant, the region of interest in the paternal genome is sequenced (optionally following targeted enrichment of the region of interest). If the genetic variant is not present in the paternal genome, and it cannot be attributed to the maternal genome (either by sequencing the corresponding region of interest in the maternal genome or by using the methods described herein), then it is a de novo genetic variant. If the genetic variant is present in the paternal genome, and it cannot be attributed to the maternal genome (either by sequencing the corresponding region of interest in the maternal genome or by using the methods described herein), then it is substantially likely to be a paternally-inherited genetic variant.

Copy Number Variant (CNV) Detection

In some embodiments, provided herein is a method of detecting the presence or absence of a genetic variant in a region of interest in the genome of a fetus in a pregnant woman, wherein the fetal genetic variant is a de novo copy number variant (such as a copy number loss variant) or a paternally-inherited copy number variant (such as a copy number loss variant). In some embodiments, the father's genome is sequenced to reveal whether the copy number variant is a paternally inherited copy number variant or a de novo copy number variant. That is, if the fetal copy number variant is not present in the father, and the described method indicates that the fetal copy number variant is distinguishable from the maternal genome, then the fetal copy number variant is a de novo copy number variant. Accordingly, provided herein is a method of determining whether a fetal copy number variant is an inherited copy number variant or a de novo copy number variant.

Cell-free DNA can be extracted from plasma of a pregnant woman (i.e., maternal plasma). The plasma comprises cell-free DNA from the fetal genome and cell-free DNA from the maternal genome. A DNA library is then formed from the cell-free DNA and the region of interest is enriched, thereby forming a population of enriched DNA molecules that correspond to the region of interest. The enriched DNA molecules are then sequenced to produce a plurality of cell-free sequencing reads. In some embodiments, molecular barcodes are employed. In some embodiments, the molecular barcodes are used to distinguish single nucleotide polymorphisms variants from random mutations.

The plurality of cell-free sequencing reads comprises sequencing reads from the fetal region of interest and sequencing reads from the maternal region of interest. An increase or decrease in the read frequency at a particular allele is computed, which indicates variance between the fetal genome and the maternal genome. A copy number variant call can be made on the basis of that variance. In some embodiments, the variance is above (in the case of an increase in read frequency) or below (in the case of a decrease in read frequency) a predetermined threshold to trigger a variant call. Variance between the fetal and maternal genome for a region of interest is generally due to either a paternally inherited chromosome or a de novo mutation.

In addition to the accurate detection of large copy number variants (such as aneuploidy), microdeletions, paternally inherited or de novo genetic variants, maternally inherited genetic variants in the fetus can be detected in methods using a maternal haplotype. In some embodiments, maternal genomic DNA is isolated from the pregnant mother, for example from leukocytes present in a buffy coat. At least one region of interest corresponding to the region of interest in the cell-free DNA is sequenced from the maternal genomic DNA. Optionally, the maternal genomic DNA is enriched at the corresponding region of interest. Also optionally, molecular barcodes are used with the maternal genomic DNA. The maternal haplotypes are then constructed, for example using molecular phasing technologies, using a sequence of a biological relative, or using statistical haplotype mapping.

An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome and is a fetal genetic variant.

Autosomal Recessive Variant Detection

In some embodiments, provided herein is a method of detecting the presence or absence of a genetic variant in a region of interest in the genome of a fetus in a pregnant woman, wherein the fetal genetic variant is an autosomal recessive fetal genetic variant. In some embodiments, the autosomal fetal genetic variant is an SNP. In some embodiments, the fetal genetic variant is a copy number variant, such as a copy number loss variant, or a microdeletion.

In some embodiments, cell-free DNA is extracted from the plasma of a pregnant woman. In some embodiments, maternal genomic DNA is also extracted, for example, from a maternal buffy coat. A DNA library comprising a plurality of DNA molecules can be prepared from the extracted cell-free DNA, which can include incorporation of oligonucleotides. The oligonucleotides can comprise, for example, one or more of site-specific sequences (i.e., for targeted enrichment), a molecular barcode, or a sequencing adapter. Optionally, in some embodiments, a maternal DNA library is prepared from maternal genomic DNA, which can also include the incorporation of oligonucleotides.

The DNA library (or DNA libraries if a maternal DNA library is included) is then analyzed at a predetermined region of interest. In some embodiments, the analysis comprises enriching DNA molecules in the DNA library for those DNA molecules which comprise the region of interest or a portion of the region of interest, for example by hybridization, followed by sequencing or digital PCR of the enriched DNA molecules. In some embodiments, the analysis comprises simultaneously enriching and sequencing the DNA molecules comprising the region of interest or a portion of the region of interest, for example by selectively sequencing DNA molecules.

In some embodiments, the sequenced DNA molecules are then aligned to generate "long reads" of the region of interest. Alternatively, the short sequencing reads can be queried for known genetic sequence variants (which would not require alignment of the sequencing reads).

In some embodiments, maternal haplotypes are constructed, for example using molecular phasing technologies, using a sequence of a biological relative, or using statistical haplotype mapping. An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome and is a fetal genetic variant.

Automation (LIMS)

In some embodiments, the assays as described herein are integrated with a laboratory information management system (LIMS), as described below.

A LIMS, also referred to as a laboratory management system (LMS) or a laboratory information system (LIS), is a system for modernizing functions within a laboratory that have traditionally been performed manually or semi-manually. A LIMS system may include but is not limited to a server or host computer, database, management software, and may be coupled to associated laboratory instrumentation for performing respective laboratory functions. A LIMS system will generally assist laboratory personnel in tracking, analyzing, sorting, and routing laboratory samples throughout complex laboratory processes in an efficient and cost-effective manner.

Advantages of LIMS systems include, but are not limited to, enhanced sample management, quality control, chain of custody, and report generation. A LIMS system also permits flexible control of access to laboratory information among a diverse user set, such as physicians, patients, analysts, and technicians.

A LIMS as disclosed herein provides for automation and laboratory information management, and may be embodied as a system, method, or computer program product.

Furthermore, the present invention may take the form of an entirely software embodiment, entirely hardware embodiment, or a combination of software and hardware embodiments. Even further, the present invention may take the form of a computer program product contained on a computer-readable storage medium, where computer-readable code is embodied on the storage medium. In another embodiment, the present invention may take the form of computer software implemented as a service (SaaS). Any appropriate storage medium may be utilized, such as optical storage, magnetic storage, hard disks, or CD-ROMs.

Figure 8:
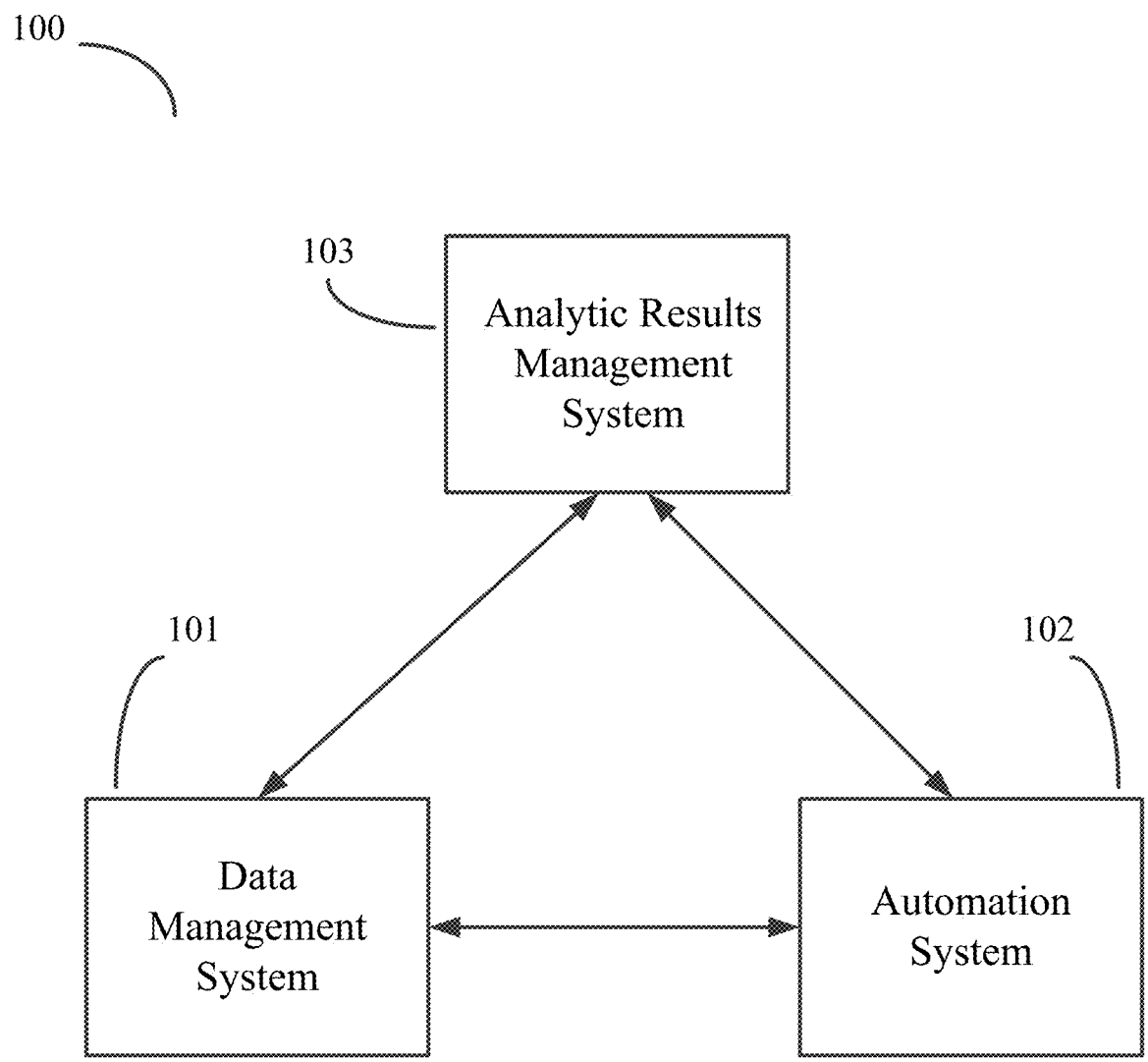
FIG. 8 illustrates an overview of an automatic diagnostic laboratory and a laboratory information management system.

FIG. 8 illustrates an overview of system 100 for an automatic diagnostic laboratory and laboratory information management system (hereinafter "LIMS"). System 100 includes a data management system 101, automation system 102, and analytics results management system (ARMS) 103. In general, data management system 101 is a centralized database tool for maintaining information pertaining to the LIMS system, such as maintaining laboratory tests, diagnostics, equipment, personnel, and the like. In one embodiment, data management system 101 is dynamically updated and facilitates the management of information among other components of the LIMS system, such as automation system 102 and ARMS 103.

Automation system 102 generally provides for the management of laboratory workflow, and may permit one or more users to create and deploy custom laboratory workflow processes. For example, automation system 102 may provide functionality for a user to create a graphical diagram to model different laboratory equipment and diagnostics, and may permit the user to customize the timing, decision-making, and other test variables of laboratory analytics. Automation system 102 may further provide functionality to permit a user to deploy one or more workflow processes based on user-generated diagrams, and such workflow processes may be modified dynamically by the user. Furthermore, automation system 102 may include hardware and software components for interfacing with laboratory equipment, such as robotics units, conveyor systems, sample repositories, climate control systems, (e.g., lighting and temperature), pneumatic systems, audio/video systems, etc.

In one embodiment, automation system 102 may include hardware and/or software for enabling one or more robotics units to perform movements related to testing laboratory samples, such as mixing, shaking, heating, cooling, picking, and/or placing or samples. For example, automation system 102 may generate and send commands to the one or more robotics units to allow the robotics units to move in three-dimensional space. Such commands may also permit the one or more robotics units to interface with a pneumatics system to utilize pressurized air for grasping and releasing one or more samples. In one embodiment, the samples may be contained in a test tube, vial, or similar container. Automation system 102 may further be configured to generate and send commands to the one or more robotics units to allow the robotics units to remove and/or replace a lid on the top of a container. For example, the one or more robotics units may be equipped with machinery capable of sensing a test tube lid, and further capable of removing the test tube lid by one or more robotic motions. Similarly, the one or more robotics units may be equipped with machinery to sense a test tube without a lid, and may perform one or more robotic motions to place and seal the test tube with a lid, for example.

ARMS 103 generally provides a system for dynamically rendering and organizing laboratory information, including but not limited to information such as diagnostic results, quality control metrics, historical test data, sample genotypes, and the like. For example, ARMS 103 may facilitate the generation of interactive data visualizations to permit one or more users to effectively oversee laboratory chemistry, algorithms, and products. ARMS 103 may also permit one or more users to perform complex analytical functions, such as analyze and manipulate quality control constraints, synthesize raw test data, and manually correct test results.

In one embodiment, one or more components of the data management system 101, automation system 102, and/or ARMS 103 may be maintained at a location local to the laboratory and associated equipment (e.g., a server room). In another embodiment, one or more components of the data management system 101, automation system 102, and/or ARMS 103 may be maintained at a location remote from the laboratory and associated equipment (e.g., a "cloud-based" system). In yet another embodiment, one or more components of the data management system 101, automation system 102, and/or ARMS 103 may be maintained in a combination of local and remote locations.

Figure 9:
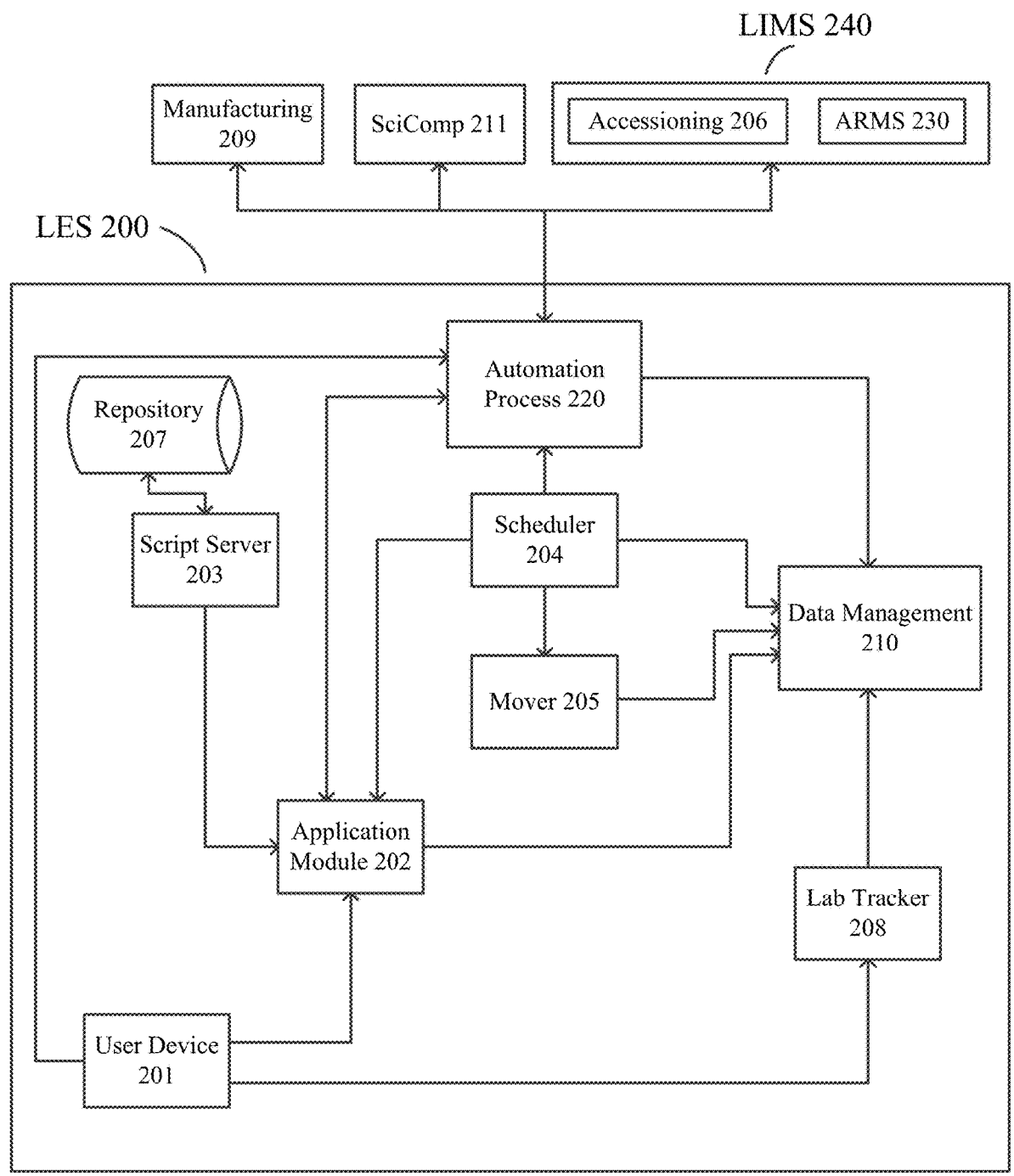
FIG. 9 illustrates a detailed view of a laboratory execution system for facilitating laboratory automation.

FIG. 9 illustrates a detailed view of a laboratory execution system (LES) 200. LES 200 may include a data management tool 210 and an automation process 220. Furthermore, LES 200 may communicate with a LIMS module 240. In one embodiment, LIMS module 240 may include at least an accessioning module 206 and an analytic results management system (ARMS) 230, which are discussed in more detail with respect to FIG. 10. FIG. 9 further depicts user device 201 and application module 202, which will now be described. User device 201 may permit a user to interact with LES 200 and thus facilitate user interaction with each of the data management tool 210, automation process 220, and ARMS 230, and/or other associated systems. User device 201 may communicate with application module 202 in order to perform one or more functions as described herein.

In one embodiment, application module 202 may be an application programming interface (API) for performing one or more automated functions. In another embodiment, application module 202 may be a graphical user interface (GUI), whereby a user may instruct LES 200 to perform one or functions such as loading a script, running a diagnostic method, executing a laboratory instrument action, or the like. User device 201 may also interface with LES 200 by direct interaction with other components of the system. For example, user 201 may provide a command directly to scheduler 204 for fixing execution time errors.

In another embodiment, lab tracker 208 facilitates physical location management of one or more robotics units. For example, lab tracker 208 may be configured as a database which stores positional information of all physical objects for a given point in time. Lab tracker 208 may also receive information from other components in LES 200. For example, user 201 may provide a command to lab tracker module 208 for fixing a plate tracking error.

FIG. 9 further depicts automation process 220, which may provide workflow management of sample plates, samples, and associated data. For example, automation process 220 may provide information regarding available plates to application module 202, or may otherwise indicate the availability of system resources to application module 202. As another example, automation process 220 may receive reporting information, such as a job completion report, from application module 202. Automation process 220 may also receive seed pipeline information, which may be manually entered by a user and provided directly to the automation process 220 from user device 201. Seed pipeline information may include, for example, information to instantiate new objects for management into the LIMS system. For example, a user may utilize a GUI in order to create research samples, where the research samples are introduced as seed pipeline information into automation process 220.

In another embodiment, automation process 220 may receive seed pipeline information from an accessioning module 206. In yet another embodiment, automation process 220 may receive query information from ARMS 230, for example, a query regarding results to be displayed. Automation process 220 may further receive query information from scheduler 204, for example, a query regarding a pending job. Furthermore, automation process 220 may provide data management tool 210 with data validation information and information regarding data queries.

Furthermore, FIG. 9 shows data management tool 210, which will now be described. Data management tool 210 may be configured to integrate quantitative data, track sample barcodes, and manage overall workflow of LES 200. In one embodiment, data management tool 210 may receive information regarding a report operation from application module 202. In another embodiment, data management tool 210 may receive a report operation from mover module 205. Furthermore, data management tool 210 may receive a command to fix plate tracking errors from a user via lab tracker module 207. In yet another embodiment, data management tool 210 may receive, from scheduler 204, a query regarding stateful data. In one example, such a query pertains to seal, spin, or location information.

FIG. 9 further depicts script server 203 and repository 207, which will now be described. In one embodiment, script server 203 may communicate with a version control system (VCS) repository 207 in order to obtain one or more software scripts for use in operating LES 200. VCS repository 207 may be maintained by known repositories such as "Github," or any other appropriate VCS repository service, as will be appreciated by one of ordinary skill in the art. In one embodiment, script server 203 may obtain software scripts from VCS repository 207, and may further push one or more software scripts to application module 202. Script server 203 may be further configured to deploy scripts and manage script metadata.

Scheduler 204 may be configured to automate scheduling and execute applications. For example, scheduler 204 may include at least one software module such as script compiler, scheduler, and/or executor. In one embodiment, scheduler 204 may provide application module 202 with one or more commands for performing an action, or may further provide application module 202 with a query for an API function. In another embodiment, scheduler 204 may be configured to initiate and/or deliver one or more queries for an API function, and may be further configured to initiate and/or deliver one or more queries regarding stateful data. In another embodiment, scheduler 204 may be configured to initiate and/or deliver one or more queries regarding a pending job. In yet another embodiment, scheduler 204 may be configured to receive a command to fix execution time errors.

Mover application 205 may be configured to communicate with one or more robotics units within a laboratory environment. For example, mover application 205 may facilitate the directing of the one or more robotics units to perform one or more movements in three-dimensional space. Mover application 205 may send instructions to the one or more robotics units regarding a movement, path, direction, or other information relating to three-dimensional space in which the one or more robotics units may perform any number of movements. In another embodiment, scheduler 204 may provide mover module 205 with one or more commands for performing a move, such as, for example, robotic movements described in detail with respect to FIG. 13.

Additionally, LES 200 may be configured to communicate with manufacturing module 209. In one embodiment, manufacturing module 209 is configured to provide LES 200 with information related to sample components, such as plastic, reagents, and the like. For example, manufacturing module 209 may assist in identifying sample components which are introduced into LES 200. In another embodiment, manufacturing module 209 may be configured to declare and generate barcode labels for one or more sample plates and sample tubes.

LES 200 may further communicate with SciComp module 211. In one embodiment, SciComp module 211 may facilitate overall automation within the LIMS system by managing the processing of all main stages, including but not limited to (i) physical sample acquisition, (ii) sequencing, (iii) raw data generation, (iv) data analysis, and (v) transfer of analyzed data to ARMS. In one example, SciComp module 211 may assist automation process 220 by querying automation process 200 for information pertaining to a next job to process. SciComp module 211 may further include components such a script server and/or scheduler for maintaining efficient job workflow. In one embodiment, SciComp module 211 may perform the necessary data analytics tasks of the LIMS system, and may run the necessary algorithms to automatically produce patient variant calls from raw data to analyzed data.

Although only one instance of each module is listed on FIG. 9 (e.g., one scheduler 204 and one mover 205), LES 200 may include one or more instances of any such module. For example, there may be two or more instances of scheduler 204, which are each associated with a specific process or device within the laboratory environment.

Figure 10:
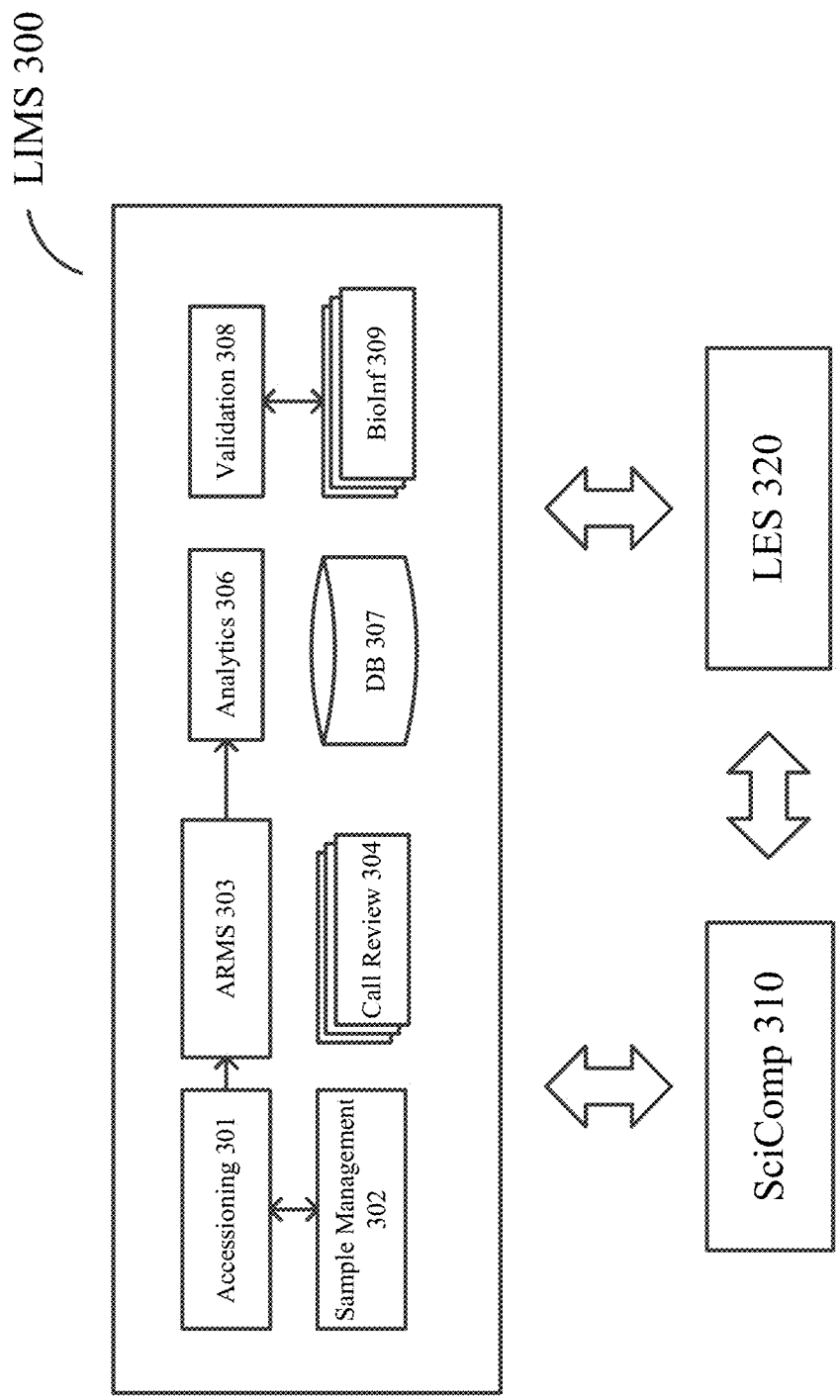
FIG. 10 illustrates a detailed view of a laboratory information management system for facilitating laboratory automation.

FIG. 10 illustrates a detailed depiction of laboratory information management system (LIMS) 300. In one embodiment, LIMS 300 includes an accessioning module 301 and sample management module 302. Accessioning module 301 may be configured to record the arrival of a sample and instantiate the arrival of the sample within one or more databases. For example, accessioning module 301 may be configured to send a first set of information to ARMS 303. The first set of information may include, for example, information pertaining to a disease panel order. Sample management module 302 may be configured to communicate with accessioning module 301 in the organization of one or more samples to be seeded to ARMS 303. Analytics module 306 may receive one or more outputs from ARMS 303, such as results pertaining to a disease panel order. LIMS 300 may further include validation module 308 and bioinformation module 309. Validation module 308 and bioinformation module 309 may each be configured to assist in the development of sample assays for testing.

As depicted in FIG. 10, LIMS 300 may further communicate with LES 310 and SciComp 320, as discussed with respect to FIG. 9. LIMS 300 may further include a call review module 304, which may be configured to provide processing techniques to review and modify variant call processing data. LIMS 300 may further include a database module 307 to store information relating to samples and associated test data, as used within LIMS 300.

ARMS 303 may be further configured as a database containing genotypes for samples. For example, ARMS 303 may be configured to process, maintain, and deliver information regarding genotyping data based on one or more Variant Call Format (VCF) files. As will be appreciated by one of ordinary skill in the art, a VCF file is a standardized text file format for representing and storing gene sequence variations. In one embodiment, ARMS 303 may provide a results query to an automation process on LES 320. For example, a results query may be utilized to determine which results are capable of being displayed.

In another embodiment, ARMS 303 includes functionality for generating a GUI, where the GUI provides a user with real-time data corresponding to laboratory diagnostics and analysis for one or more samples. The GUI may permit the user to perform a plurality of functions, including but not limited to quality control (QC) monitoring and adjustment, sample history generation, manual tagging of samples, and the ability to manually pass or fail a given sample. ARMS 303 may include functionality for generating custom diagnostics reports, including the generation of graphs, tables, spreadsheets, plots, diagrams, and/or other visualization to enable efficient data interpretation.

Figure 11:
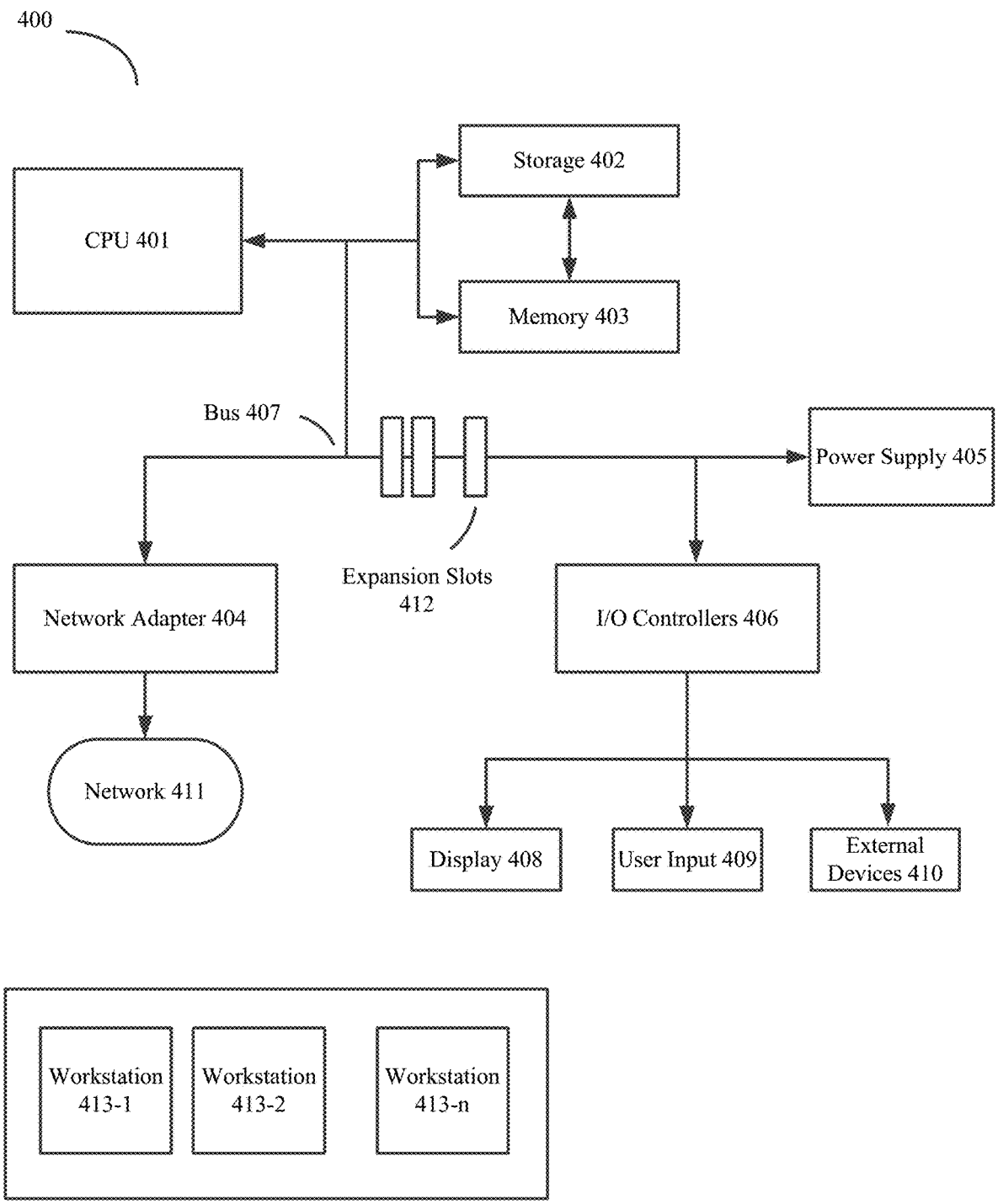
FIG. 11 illustrates a general computing system in which one or more systems may be implemented.

FIG. 11 illustrates a general purpose computing system 400 in which one or more systems, as described herein, may be implemented. System 400 may include, but is not limited to known components such as central processing unit (CPU) 401, storage 402, memory 403, network adapter 404, power supply 405, input/output (I/O) controllers 406, electrical bus 407, one or more displays 408, one or more user input devices 409, and other external devices 410. It will be understood by those skilled in the art that system 400 may contain other well-known components which may be added, for example, via expansion slots 412, or by any other method known to those skilled in the art. Such components may include, but are not limited to, hardware redundancy components (e.g., dual power supplies or data backup units), cooling components (e.g., fans or water-based cooling systems), additional memory and processing hardware, and the like.

System 400 may be, for example, in the form of a client-server computer capable of connecting to and/or facilitating the operation of a plurality of workstations or similar computer systems over a network. In another embodiment, system 400 may connect to one or more workstations over an intranet or internet network, and thus facilitate communication with a larger number of workstations or similar computer systems. Even further, system 400 may include, for example, a main workstation or main general purpose computer to permit a user to interact directly with a central server. Alternatively, the user may interact with system 400 via one or more remote or local workstations 413. As will be appreciated by one of ordinary skill in the art, there may be any practical number of remote workstations for communicating with system 400.

CPU 401 may include one or more processors, for example Intel® Core™ i7 processors, AMD FX™ Series processors, or other processors as will be understood by those skilled in the art. CPU 401 may further communicate with an operating system, such as Windows NT® operating system by Microsoft Corporation, Linux operating system, or a Unix-like operating system. However, one of ordinary skill in the art will appreciate that similar operating systems may also be utilized. Storage 402 may include one or more types of storage, as is known to one of ordinary skill in the art, such as a hard disk drive (HDD), solid state drive (SSD), hybrid drives, and the like. In one example, storage 402 is utilized to persistently retain data for long-term storage. Memory 403 may include one or more types memory as is known to one of ordinary skill in the art, such as random access memory (RAM), read-only memory (ROM), hard disk or tape, optical memory, or removable hard disk drive. Memory 403 may be utilized for short-term memory access, such as, for example, loading software applications or handling temporary system processes.

As will be appreciated by one of ordinary skill in the art, storage 402 and/or memory 403 may store one or more computer software programs. Such computer software programs may include logic, code, and/or other instructions to enable processor 401 to perform the tasks, operations, and other functions as described herein, and additional tasks and functions as would be appreciated by one of ordinary skill in the art. Operating system 402 may further function in cooperation with firmware, as is well known in the art, to enable processor 401 to coordinate and execute various functions and computer software programs as described herein. Such firmware may reside within storage 402 and/or memory 403.

Moreover, I/O controllers 406 may include one or more devices for receiving, transmitting, processing, and/or interpreting information from an external source, as is known by one of ordinary skill in the art. In one embodiment, I/O controllers 406 may include functionality to facilitate connection to one or more user devices 409, such as one or more keyboards, mice, microphones, trackpads, touchpads, or the like. For example, I/O controllers 406 may include a serial bus controller, universal serial bus (USB) controller, FireWire controller, and the like, for connection to any appropriate user device. I/O controllers 406 may also permit communication with one or more wireless devices via technology such as, for example, near-field communication (NFC) or Bluetooth™. In one embodiment, I/O controllers 406 may include circuitry or other functionality for connection to other external devices 410 such as modem cards, network interface cards, sound cards, printing devices, external display devices, or the like. Furthermore, I/O controllers 406 may include controllers for a variety of display devices 408 known to those of ordinary skill in the art. Such display devices may convey information visually to a user or users in the form of pixels, and such pixels may be logically arranged on a display device in order to permit a user to perceive information rendered on the display device. Such display devices may be in the form of a touch-screen device, traditional non-touch screen display device, or any other form of display device as will be appreciated be one of ordinary skill in the art.

Furthermore, CPU 401 may further communicate with I/O controllers 406 for rendering a graphical user interface (GUI) on, for example, one or more display devices 408. In one example, CPU 401 may access storage 402 and/or memory 403 to execute one or more software programs and/or components to allow a user to interact with the system as described herein. In one embodiment, a GUI as described herein includes one or more icons or other graphical elements with which a user may interact and perform various functions. For example, GUI 407 may be displayed on a touch screen display device 408, whereby the user interacts with the GUI via the touch screen by physically contacting the screen with, for example, the user's fingers. As another example, GUI may be displayed on a traditional non-touch display, whereby the user interacts with the GUI via keyboard, mouse, and other conventional I/O components 409. GUI may reside in storage 402 and/or memory 403, at least in part as a set of software instructions, as will be appreciated by one of ordinary skill in the art. Moreover, the GUI is not limited to the methods of interaction as described above, as one of ordinary skill in the art may appreciate any variety of means for interacting with a GUI, such as voice-based or other disability-based methods of interaction with a computing system.

Moreover, network adapter 404 may permit device 400 to communicate with network 411. Network adapter 404 may be a network interface controller, such as a network adapter, network interface card, LAN adapter, or the like. As will be appreciated by one of ordinary skill in the art, network adapter 404 may permit communication with one or more networks 411, such as, for example, a local area network (LAN), metropolitan area network (MAN), wide area network (WAN), cloud network (IAN), or the Internet.

One or more workstations 413 may include, for example, known components such as a CPU, storage, memory, network adapter, power supply, I/O controllers, electrical bus, one or more displays, one or more user input devices, and other external devices. Such components may be the same, similar, or comparable to those described with respect to system 400 above. It will be understood by those skilled in the art that one or more workstations 413 may contain other well-known components, including but not limited to hardware redundancy components, cooling components, additional memory/processing hardware, and the like.

Figure 12:
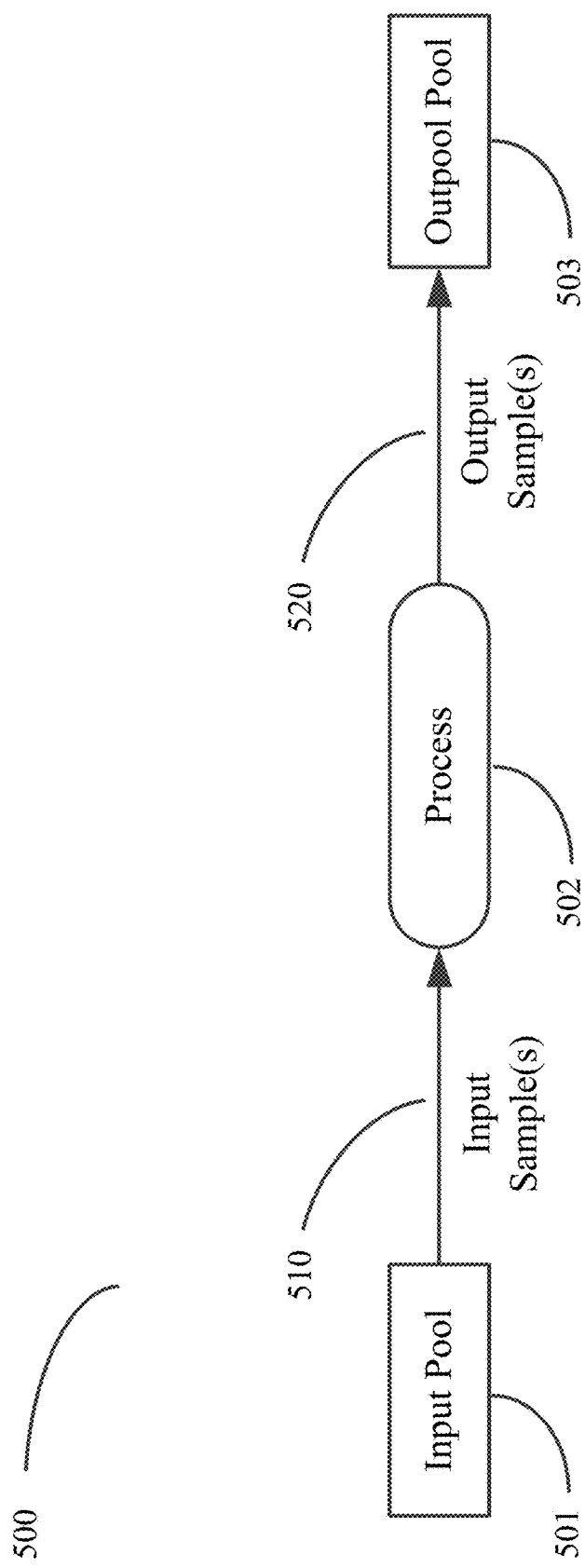
FIG. 12 illustrates an exemplary workflow diagram for sample processing.

FIG. 12 illustrates an exemplary laboratory process 500 facilitated by, for example, automation process 220 in FIG. 9. In one embodiment, automation process 220 provides a user with the ability to create lab workflow processes in order to maintain sample queues for diagnostics and analysis. For example, a user may create one or more graphical objects on a GUI display, where the objects may represent one or more laboratory states, decisions, inputs, outputs, or other conditions to model a laboratory process. A resulting laboratory process may be created based on the one or more graphical objects created by the user, such as, for example, a process as depicted in FIG. 12.

In one embodiment, process 500 includes input pool object 501, which may represent, for example, one or more polymerase chain reaction (PCR) plates. Samples from the input pool may be scheduled to undergo one or more tests, diagnostics, or other laboratory processes 502. For example, samples within the one or more PCR plates may undergo a process for DNA amplification. Arrow 510 may represent the transfer of one PCR plate 501 to amplification process 502, for example. Arrow 520 may represent a successful output of amplification process 502, such as, for example, one amplified PCR plate. Output pool 503 may represent, for example, one or more amplified PCR plates. Arrow 520 may therefore represent the transfer of one amplified PCR plate to output pool object 503. Although only one input, one process, and one output are depicted in process 500, it will be appreciated that any number of inputs, outputs, processes, transfers, or other laboratory functions may be represented by such a graphical diagram, and that the invention is not limited to the exemplary process depicted in FIG. 12.

Figure 13:
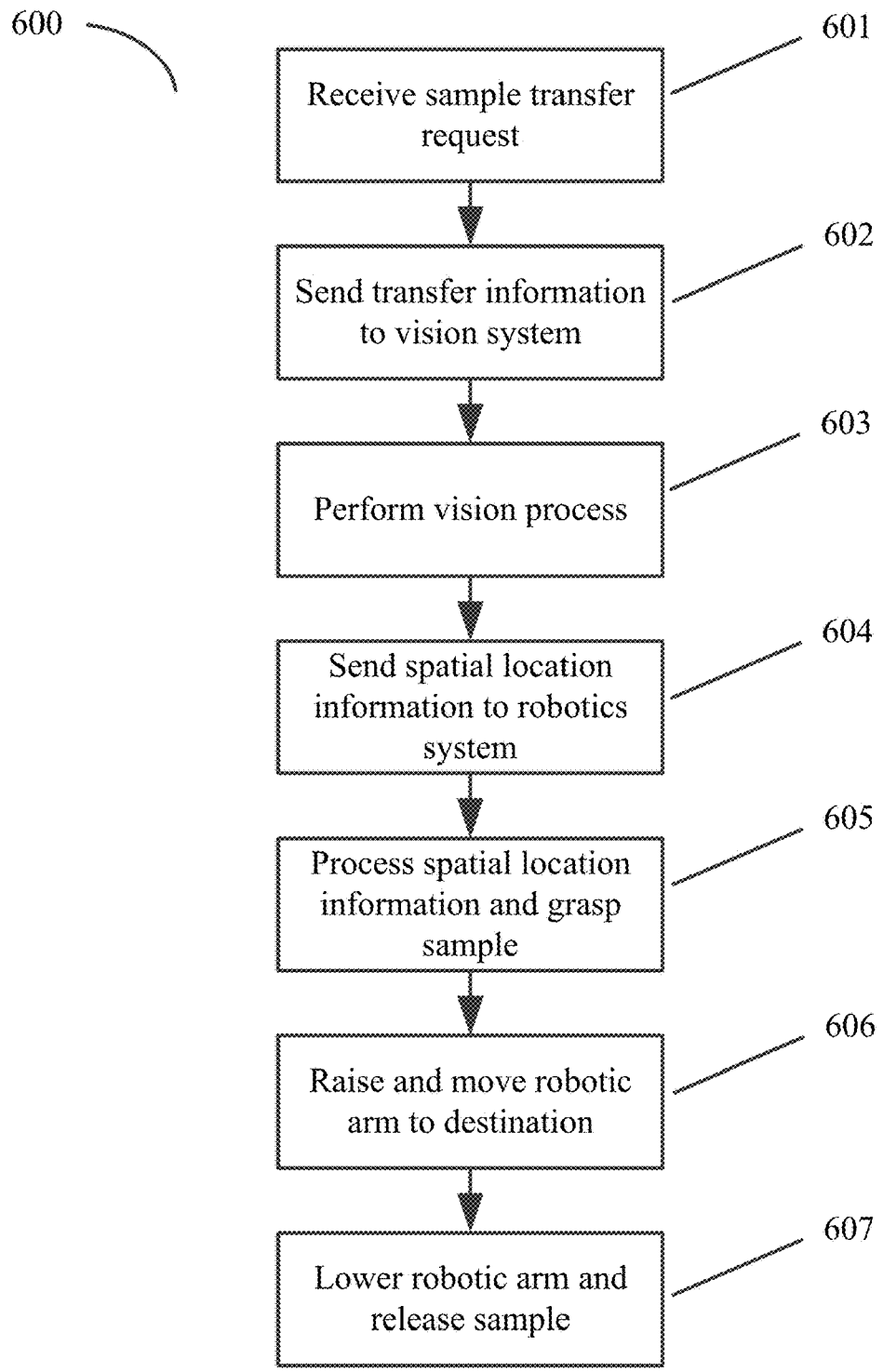
FIG. 13 illustrates an exemplary process for controlling a robotics unit to transport one or more sample tubes.

FIG. 13 illustrates an exemplary transfer process 600 for controlling a robotics unit to transport one or more sample tubes. Transfer process 600 may be facilitated at least in part by automation process 220 as described in FIGS. 13 and 14. For example, automation process 220 may communicate with hardware and software processes associated with one or more robotics, vision, and/or pneumatic systems in order to perform transfer process 600. In one embodiment, transfer process 600 is utilized to transfer at least one sample from an origin location to a destination location by using at least one robotics unit coupled with vision and pneumatics systems.

Transfer process 600 may begin at step 601, where automation process may receive a sample transfer request. Such request may be, for example, a manual request entered by a user, or may be an automated request initiated by a pre-scheduled workflow process. In one embodiment, the request includes information identifying at least one sample barcode corresponding to a current sample, and may further include information identifying a destination location for transferring the sample associated with the sample barcode from an origin location to the destination location.

At step 602, automation process may send transfer information to a vision system in order to identify the spatial location of the identified sample. In one embodiment, the vision system performs a vision matching process at step 603 to identify if a matching barcode exists within the vision system's viewing area. If a matching barcode is found, the vision system may send corresponding spatial location information to robotics system at step 604. Such spatial location information may correspond to sample location information discovered by the vision system when identifying matching barcode in step 603. The spatial location information may be in a form readable by robotics unit in order to permit the robotics unit to identify a three dimensional location in space corresponding to the physical sample identified.

At step 605, the robotics unit may receive and process the spatial location information, and may further grasp the identified sample. For example, the robotics unit may utilize the spatial location information to move a robotic arm to a location corresponding to a position directly above the identified sample. The robotic arm may then be lowered to a location near the sample, and the arm may grasp the sample by utilizing, for example, a pneumatic system. In one example, the sample is contained in a test tube which is grasped by a robotic arm, where a pneumatic system generates a vacuum in order to grip the test tube.

At step 606, the robotic arm may be raised while grasping the sample, and the robotic arm may be moved to a location corresponding to a destination location as received in the sample transfer request. At step 607, the robotic arm may lower the sample onto a location corresponding to the desired location, and may release the sample from the robotic grip by performing one or more pneumatic processes via the pneumatic system. For example, the pneumatic system may release the grip on the sample by discharging the vacuum and briefly expelling air near the sample.

Figure 14:
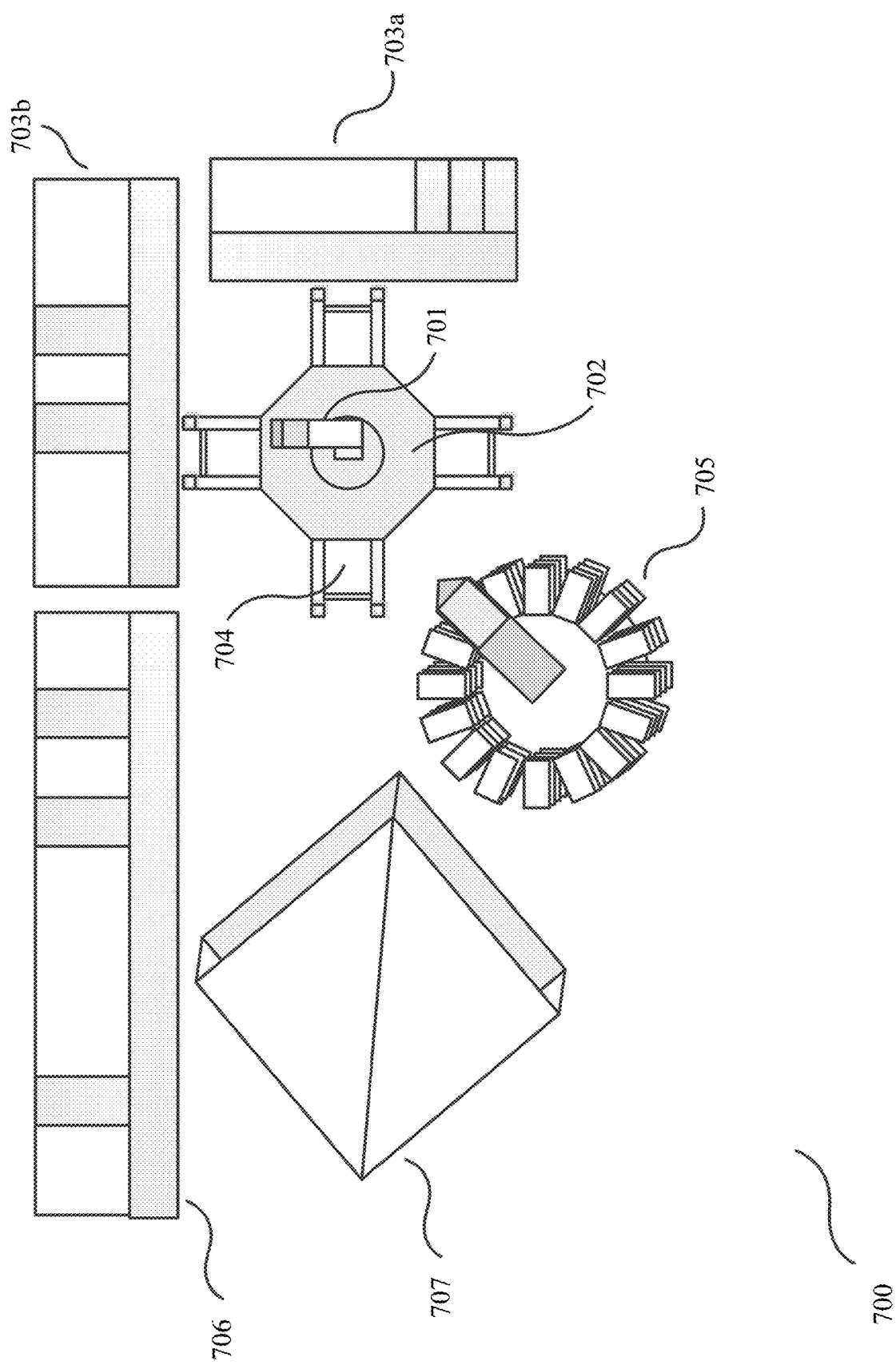
FIG. 14 illustrates a robotic system for managing automatic laboratory processes.

FIG. 14 illustrates a robotic system 700 for managing automatic laboratory processes. In one embodiment, robotic system 700 includes a robotic arm 701 for facilitating the movement of one or more samples. For example, robotic arm 701 may be configured to grasp a test tube containing a sample, and transport the test tube from a first location to a second location. In another example, robotic arm 701 may be configured to grasp a sample rack, and transport the sample rack from a first location to a second location. A sample rack may contain one or more samples, and may be stored, for example, in a sample rack repository 705. In one embodiment, sample rack repository 705 may contain one or more sample racks and may facilitate efficient storage and retrieval of one or more sample racks.

In one embodiment, robotic arm 701 may further be affixed to a robotic arm base 702, and may be configured to rotate in a 360 degree motion about the laboratory environment. For example, robotic arm 701 may extend from a first position, such as the position depicted in FIG. 14, to a second position, such as a position extending into a first liquid handling apparatus 703a. Furthermore, robotic arm 701 may, for example, retract from the extended position in first liquid handling apparatus 703a and return to the position as depicted in FIG. 14. Furthermore, robotic arm 701 may retract from the position in first liquid handling apparatus 703a, and then extend to a position within a second liquid handling apparatus 703b. In one embodiment, the robotic arm may perform various movements within liquid handling apparatus 703a and liquid handling apparatus 703b in order to facilitate various sample test procedures.

In another embodiment, robotic arm 701 may be configured to transport one or more samples and/or sample racks from sample rack repository 705 to liquid handling apparatus 703a or liquid handling apparatus 703b. Robotic arm 701 may further be configured to return one or more samples and/or sample racks from liquid handling apparatus 703a or liquid handling apparatus 703b to sample rack repository 705, for example. Furthermore, although only two liquid handling apparatus 703a and 703b are depicted in FIG. 14, one will appreciate that additional liquid handling apparatus may be deployed within the laboratory environment, and that robotic arm 701 may extend into other such areas within the reach of robotic arm 701.

In yet another embodiment, robotic arm 701 may be surrounded by one or more sensors 704. Sensors 704 may, for example, detect specific motions within an area surrounding robotic arm 701, such as a predefined motion detection area. In one embodiment, the motion detection area may be defined by a spherical or semi-spherical region centered at or near a coupling point of robotic arm 701 to robotic arm base 702. In another embodiment, the motion detection area may be defined by a spherical or semi-spherical region centered at or near a specific point in space defined by a user. For example, the motion detection area may be dynamically configured and updated by a user, and may define custom three-dimensional areas in space surrounding robotic arm 701.

Sensors 704 may, for example, provide signals to one or more software systems within the laboratory environment in order to prevent robotic arm 701 from moving into specific areas within the laboratory environment. In one example, sensors 704 may be configured to detect movements associated with a user or other object within a specified motion detection area near robotic arm 701. If sensors 704 detect such motions, sensors 704 may send one or more alarm signals to software systems associated with robotic arm 701 in order to cease all movements of robotic arm 701. Sensors 704 may be configured to, for example, send signals to software systems associated with robotic arm 701 in order to resume movements of robotic 701 upon the sensors 704 detecting that any such user, object, or other event causing the alarm signals is no longer within the motion detection area. In another embodiment, sensors 704 and robotic arm 701 may remain disabled after the alarm signal until a predefined user restart process is initiated and completed. Upon completion of such user restart process, the robotic arm 701 and sensors 704 may, for example, resume normal operations.

In another embodiment, robotic system 700 includes an additional liquid handling apparatus 706 having a robotics unit configured for automated DNA extraction. Liquid handling apparatus 706 may be configured to handle multiple tube sizes and/or multiple sample types. For example, liquid handling apparatus 706 may be configured to handle either a 4 mm tube size or a 6 mm tube size. In another example, liquid handling apparatus 706 may be configured to handle either a blood sample or a saliva sample. In another embodiment, robotic system 700 includes a robotic refrigerator 707, which may be configured to store and retrieve sample plates of one or more different sizes. Robotic refrigerator 707 may be further configured, for example, to allow for human override to permit manual access to the contents within robotic refrigerator 707.

Figure 15:
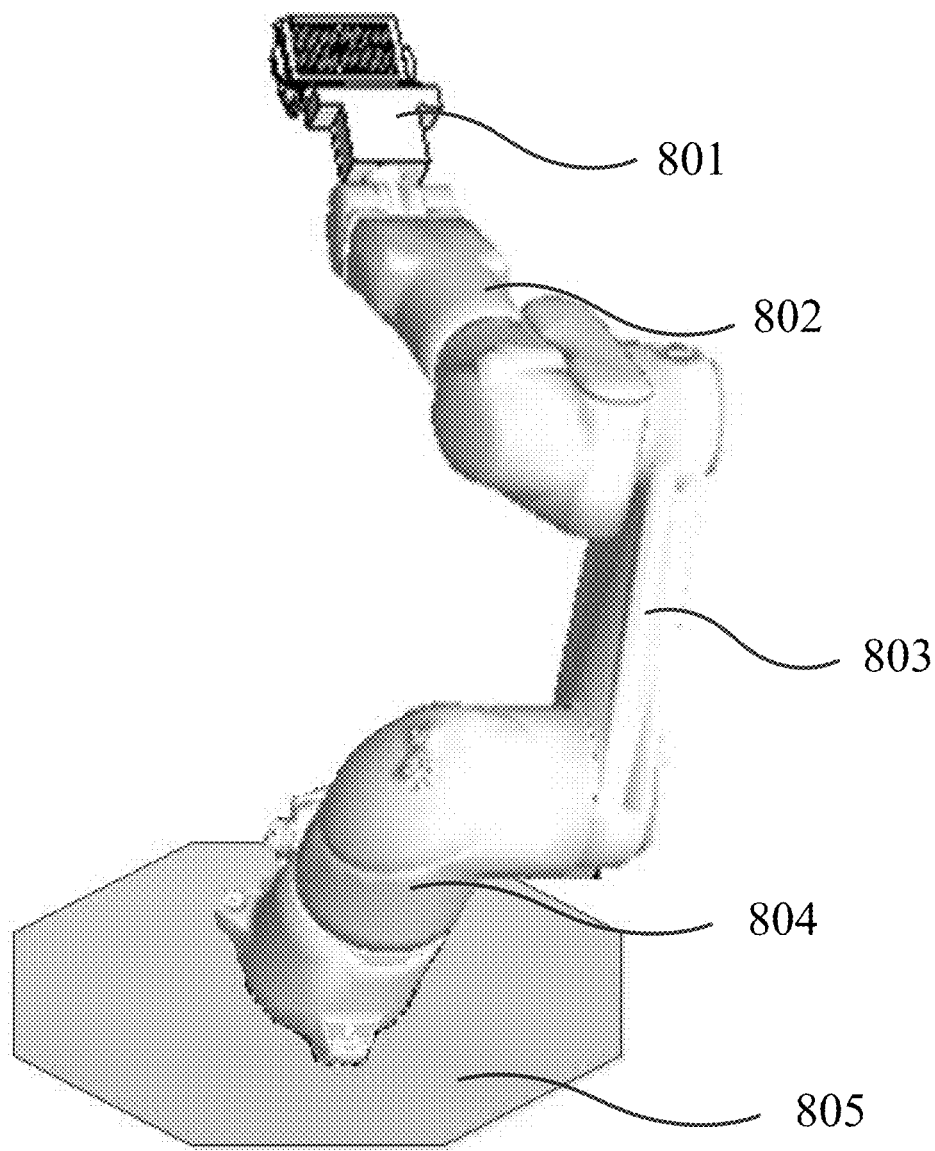
FIG. 15 illustrates an angled view of a robotic arm.
Figure 15:
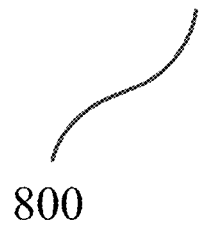

FIG. 15 illustrates an angled view of a robotic arm 800, for example, a robotic arm such as robotic arm 701 in FIG. 14. As depicted in FIG. 15, robotic arm 800 includes a sample handling portion 801, a first solid section 802, a second solid section 803, a third solid section 804, and a robotic arm base 805. In one embodiment, sample handling portion 801 is connected to the first solid section 802. In another embodiment, first solid section 802 is connected at one end to sample handling portion 801, and is connected at another end to second solid section 803. In yet another embodiment, second solid section 803 is connected at one end to first solid section 802, and is connected at another end to third solid section 804. In yet another embodiment, third solid section 804 is connected at one end to second solid section 803, and is connected at another end to robotic arm base 805.

Tube Picker

Tube sorting devices have been previously described. For example, see U.S. patent application Ser. No. 15/388,193 filed 22 Dec. 2017, entitled "Robotic System for Sorting Sample Tubes".

Tube sorting devices include a robotic arm for picking up a tube from a first location in a first sample tube rack and sorting the tube to a second location in the first sample tube rack or in a second sample tube rack. The initial loading of tubes in the first tube rack may be manual or may utilize a second robotic arm, e.g., including an interface between another robotic system and the tube sorting device. Use of a robotic system as disclosed herein improves speed of sorting, permitting, for example, sorting of greater than 10, 20, 30, or 40 tubes per minute. The tubes may be sample tubes, i.e., tubes containing a patient sample, or an assay reagent tube, i.e., a tube containing a reagent useful in as assay as described herein. In one embodiment, the tube is an assay reagent tube containing a probe or primer.

Use of the tube picker allows the rapid customization of the probe panel. The selection of a plurality of probes from a panel of prepared probes can be done quickly. The selection of the plurality of probes may be done in minutes and the tubes containing each of the probes is selected, sorted and sent to the station that will combine an aliquot of the probes such that the plurality of probes is unique for the sample being tested.

The tube picker enables the rapid creation of large probe panels and removes the limitation of manually preparing the panels. Once the selected probes are determined, the tube picker allows the rapid placement of the correct tubes in a rack for preparation of the signature panel.

Assay Methods herein generally comprise the following steps:
A) Screening a specimen, e.g., a sample, to identify a genetic signature composed of segregating markers.
B) Designing a personalized/unique reagent, e.g., probes, for detecting said signature/markers.
C) Screening an "unknown" specimen using the personalized/unique reagent to determine the extent at which the signature is present.

The methods are described herein detecting the presence of unique genetic signature. The methods find use in, for example, cancer related applications. However, it will be understood that a non-invasive prenatal test is also possible when the paternal and/or maternal genomic profile(s) is/are known. For example, when each parent is a carrier for a disease such that if the fetus inherited a copy of the carrier allele from each parent it would be affected then an assay based on the known parental genomic information can be performed in a manner analogous to the cancer based assay. The assays described herein also find use in forensic DNA analysis. For example, to identify a particular person, e.g., an individual subject or suspect, in a test sample comprising a mixture of DNA from multiple sources, i.e., when there is more than one contributor found in a biological sample, then an assay based on the particular person's DNA using a unique combination of probes specific for the individual.

Phase I—Signature Panel of Markers/Mutations and Capture Probes

Signature Panel of Mutations/Markers

In some embodiments, sequencing of the nucleic acid from the sample is performed using whole genome sequencing (WGS). In some embodiments, targeted sequencing is performed and may be either DNA or RNA sequencing. The targeted sequencing may be to a subset of the whole genome. In some embodiments the targeted sequencing is to introns, exons, non-coding sequences or a combination thereof. In other embodiments, targeted whole exome sequencing (WES) of the DNA from the sample is performed. The DNA is sequenced using a next generation sequencing platform (NGS), which is massively parallel sequencing. NGS technologies provide high throughput sequence information, and provide digital quantitative information, in that each sequence read that aligns to the sequence of interest is countable. In certain embodiments, clonally amplified DNA templates or single DNA molecules are sequenced in a massively parallel fashion within a flow cell (e.g., as described in Volkerding et al. Clin Chem 55:641-658 [2009];

Metzker M Nature Rev 11:31-46 [2010]; and WO 2014/015084). In addition to high-throughput sequence information, NGS provides quantitative information, in that each sequence read is countable and represents an individual clonal DNA template or a single DNA molecule. The sequencing technologies of NGS include pyrosequencing, sequencing-by-synthesis with reversible dye terminators, sequencing by oligonucleotide probe ligation and ion semiconductor sequencing. DNA from individual samples can be sequenced individually (i.e., singleplex sequencing) or DNA from multiple samples can be pooled and sequenced as indexed genomic molecules (i.e., multiplex sequencing) on a single sequencing run, to generate up to several hundred million reads of DNA sequences. Commercially available platforms include, e.g., platforms for sequencing-by-synthesis, ion semiconductor sequencing, pyrosequencing, reversible dye terminator sequencing, sequencing by ligation, single-molecule sequencing, sequencing by hybridization, and nanopore sequencing. Platforms for sequencing by synthesis are available from, e.g., Illumina, 454 Life Sciences, Helicos Biosciences, and Qiagen. Illumina platforms can include, e.g., Illumina's Solexa platform, Illumina's Genome Analyzer, and are described in Gudmundsson et al (Nat. Genet. 2009 41:1122-6), Out et al (Hum. Mutat. 2009 30:1703-12) and Turner (Nat. Methods 2009 6:315-6), U.S. Patent Application Pub nos. U520080160580 and U520080286795, U.S. Pat. Nos. 6,306,597, 7,115,400, and 7,232,656. 454 Life Science platforms include, e.g., the GS Flex and GS Junior, and are described in U.S. Pat. No. 7,323,305. Platforms from Helicos Biosciences include the True Single Molecule Sequencing platform. Ion Torrent, an alternative NGS system, is available from ThermoScientific and is a semiconductor based technology that detects hydrogen ions that are released during polymerization of nucleic acids. Any detection method that allows for the detection of segregatable markers may be used with the assay provided for herein.

In some embodiments, DNA can be obtained from fresh tissue such as that obtained from a biopsy of an unresected primary tumor and/or from a metastatic mass. In other embodiments, the DNA can be obtained from formalin-fixed, paraffin-embedded (FFPE) tissue. FFPE tissue has been shown to be a suitable substrate for NGS sequencing and analysis, and it opens clinical and archival specimens to high-throughput sequencing approaches for analysis of the full spectrum of DNA mutations (Duncavage et al. J Mol Diagn 13:325-333 [2011]). In yet other embodiments, the tumor DNA can be obtained from banked frozen tissue. In some embodiments, the sample is a blood sample comprising cell free fetal DNA.

Normal tissue, i.e., non-tumor tissue, is obtained from the same patient, and can be a fresh normal tissue biopsy sample, a normal FFPE sample, or a normal frozen sample. In some embodiments, the normal sample is a matched tissue sample, i.e., a sample obtained from the non-tumor portion of the same tissue from which the tumor sample is obtained. In other embodiments, the normal sample can be obtained from a tissue that is different from that from which the tumor sample was obtained, i.e., a non-matched tissue sample. In yet other embodiments, the normal sample can be obtained from normal blood cells.

DNA is extracted from both the tumor and the normal tissue samples, and sequenced in a massively parallel fashion using any one of the next generation sequencing methods (NGS) as described above. Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation.

In some illustrative embodiments, the sample DNA obtained from tumor tissue and normal tissue is cellular genomic DNA, which is subjected to fragmentation into fragments of approximately 300 or more, approximately 400 or more, or approximately 500 or more base pairs, and to which NGS methods can be readily applied.

In some embodiments, whole genome sequencing (WGS) of the tumor and normal DNA is performed. In some embodiments, WGS is performed on maternal samples. In some embodiments, WGS is performed on paternal samples.

In other embodiments, Whole Exome Sequencing (WES) of the tumor and normal DNA is performed. WES comprises selecting DNA sequences that encode proteins, and sequencing that DNA using any high throughput DNA sequencing technology. Methods that can be used to target exome DNA include the use of polymerase chain reaction (PCR), molecular inversion probes (MIP), hybrid capture, and in-solution capture. The utility of targeted genome approaches is well established, and commercially available methods for WES include the Roche NimbleGen Capture Array (Roche NimbleGen Inc., Madison, WI), Agilent SureSelect (Agilent Technologies, Santa Clara, CA), and RainDance Technologies emulsion PCR (RainDance Technologies, Lexington, MA), IDT xGen® Exome Research Panel and others.

In yet other embodiments, targeted sequencing can be focused on a select set of genes, gene regions, or amplicons that have known associations with cancer or an inherited disease. In some embodiments, fixed or commercially available panels that contain known cancer-associated genes can be used. In other embodiments, design custom panels of known cancer-associated genes can be used.

The sequences obtained for the tumor and normal tissue samples of the patient are compared, and somatic mutations that are present only in the tumor DNA are identified, and noted for use in creating a signature panel of markers, i.e., somatic mutations, that are specific for the patient. A plurality of somatic mutations that are unique to the patient are identified to create a patient specific signature panel of markers, i.e., somatic mutations. In some embodiments, the set of somatic mutations identified from the comparison of the patient's normal and tumor DNA can include greater than 50, up to 100, up to 200, up to 300, up to 400, up to 500, up to 600, up to 700, up to 800, up to 900, up to 1,000, up to 1,500, up to 2,000, up to 2,500, up to 3,000, up to 4,000, up to 5,000, up to 6,000, up to 7,000, up to 8,000, up to 9,000, up to 10,000, up to 11,000, up to 12,000, up to 13,000, up to 14,000, up to 15,000, or more than 15,000 mutations. In other embodiments, the set of unique mutations identified from the comparison of the patients' normal and tumor DNA includes between 50 and 15,000 mutations, between 100 and 15,000 mutations, between 500 and 13,000 mutations, between 1,000 and 10,000 mutations, between 2,000 and 8,000 mutations, or between 4,000 and 6,000 mutations.

Markers, e.g., mutations, can be identified by comparing sample DNA with a reference sequence, e.g., human reference genome. Somatic mutations that can be identified by comparing sequences from normal and tumor tissue include single base pair changes, e.g., single nucleotide polymorphisms (SNPs), multiple nucleotide polymorphisms, insertions, deletions, and inversions. Identification of somatic mutations is performed by aligning sequence reads to a reference genome, e.g., hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, about 500 bp, or more than 500 bp.

Subsequently, a subset or all of the identified patient-specific somatic mutations is chosen to provide a signature panel of mutations that are specific to the patient, and that can be interrogated repeatedly. The signature panel can be interrogated, for example, at different times to monitor regression of disease, at different times to monitor progression of disease, at different times to detect relapse following remission. The panel of mutations can also be interrogated at times following, coinciding with and/or prior to surgery, following, during and/or prior to chemotherapy, following, during and/or prior to radiation therapy. The panel of markers, e.g., mutations, can also be interrogated at times prior to, coinciding with, and/or following an imaging test, such as a PET scan, a PET/CT scan, an MRI, or an X-ray.

In some embodiments, the signature panel of markers, e.g., mutations, that can be interrogated for the patient can be a unique set of somatic mutations that are specifically identified in the patient's genome. The signature panel of markers is a set of a mixture of somatic mutations that are known to be associated with the patient's disease, and somatic mutations present in the patient's genome that are not known to be associated with the patient's disease. In yet other embodiments, the signature panel of markers can be a set of somatic mutations that are currently known to be associated with the patient's disease. Signature panels can be sets of somatic mutations that can are known to be associated with a number of diseases, including cancer, neurodegenerative disease, infectious diseases, autoimmune diseases, anemia and cystic fibrosis.

In some embodiments, the signature panel is a set of somatic mutations that have been identified in a tumor of a cancer patient. In some embodiments, the signature panel can be a set of somatic mutations that are known to be associated with any one of a variety of solid tumors, including metastatic tumors of blood-borne cancers, e.g., lymphomas. In other embodiments, the signature panel is a set of mutations that have been identified in the cancer patient but are not somatic mutations that are known to be associated with the type of cancer of the patient who is being tested. In yet other embodiments, the signature panel is a set of a mixture of somatic mutations known to be associated with the type of cancer suffered by the patient and somatic mutations that are not known to be associated with the patient's type of cancer.

In some embodiments, the signature panel is a set of mutations that have been identified in the maternal and/or paternal genome(s) of a fetus.

Types of cancers that can be detected and/or monitored according to the method provided include, but are not limited to, adrenal cancer, anal cancer, bile duct cancer, bladder cancer, bone cancer, brain/CNS tumors in adults, Brain/CNS Tumors In Children, Breast cancer, Breast cancer In Men, cancer in Adolescents, cancer in Children, cancer in Young Adults, cancer of Unknown Primary, Castleman Disease, Cervical cancer, Colon/Rectum cancer, Endometrial cancer, Esophagus cancer, Ewing Family Of Tumors, Eye cancer, Gallbladder cancer, Gastrointestinal Carcinoid Tumors, Gastrointestinal Stromal Tumor (GIST), Gestational Trophoblastic Disease, Hodgkin Disease, Kaposi Sarcoma, Kidney cancer, Laryngeal and Hypopharyngeal cancer, Leukemia, Leukemia—Acute Lymphocytic (ALL) in Adults, Leukemia—Acute Myeloid (AML), Leukemia—Chronic Lymphocytic (CLL), Leukemia—Chronic Myeloid (CML), Leukemia—Chronic Myelomonocytic (CMML), Leukemia in Children, Liver cancer, Lung cancer, Lung cancer—Non-Small Cell, Lung cancer—Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus cancer, Nasopharyngeal cancer, Neuroblastoma, Non-Hodgkin Lymphoma, Non-Hodgkin Lymphoma In Children, Oral Cavity and Oropharyngeal cancer, Osteosarcoma, Ovarian cancer, Pancreatic cancer, Penile cancer, Pituitary Tumors, Prostate cancer, Retinoblastoma, rhabdomyosarcoma, Salivary Gland cancer, Sarcoma—Adult Soft Tissue cancer, Skin cancer, Skin cancer—Basal and Squamous Cell, Skin cancer—Melanoma, Skin cancer—Merkel Cell, Small Intestine cancer, Stomach cancer, Testicular cancer, Thymus cancer, Thyroid cancer, Uterine Sarcoma, Vaginal cancer, Vulvar cancer, Waldenstrom macroglobulinemia, and Wilms Tumor.

Capture Probes

The signature panel is represented by a set of oligonucleotide capture probes each designed to at least partially hybridize to a target sequence that has been identified to comprise the mutation identified in the tumor sample from the patient or in the parental sequence. In some embodiments, the signature panel comprises capture probes comprising the somatic mutations identified in the patient's tumor, and capture probes of the corresponding unmutated sequence, i.e., normal target sequence. In some embodiments, the capture probe is designed to selectively hybridize to the target sequence. The capture probe can be at least 70%, 75%, 80%, 90%, 95%, or more than 95% complementary to a target sequence. In some embodiments, the capture probe is 100% complementary to a target sequence. In some embodiments the capture probes are DNA probes. In other embodiments, the capture probes can be RNA (Gnirke et al. "Solution hybrid selection with ultra-long oligonucleotides for massively parallel sequencing" published in Nature Biotechnology 2009 February; 27(2):182-9. doi: 10.1038/nbt.1523. Epub 2009 Feb. 1, which is herein incorporated by reference in its entirety.

The capture probe generally is sufficiently long to encompass the sequence of the somatic mutation, or corresponding normal sequence comprised in the genomic sequence targeted by the capture probe. The length and composition of a capture probe can depend on many factors including temperature of the annealing reaction, source and base composition of the oligonucleotide, and the estimated ratio of probe to genomic target sequence. Additionally, the length of the capture probe is dependent on the length of the target sequence it is designed to capture. The method provided utilizes cell free DNA (cfDNA) including circulating tumor DNA (ctDNA) as the source of the target sequences that are to be captured. Accordingly, as cfDNA is highly fragmented to an average of about 170 bp, the capture probe can be, for example, between 100 and 300 bp, between 150 and 250 bp, or between 175 and 200 bp. Currently, methods known in the art describe probes that are typically longer than 120 bases. In a current embodiment, if the allele is one or a few bases then the capture probes may be less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases, and this is sufficient to ensure equal enrichment from all alleles. When the mixture of DNA that is to be enriched using the hybrid capture technology is a mixture comprising cfDNA isolated from blood the average length of DNA is quite short, typically less than 200 bases. The use of shorter probes results in a greater chance that the hybrid capture probes will capture desired DNA fragments. Larger variations may require longer probes. In an embodiment, the variations of interest are one (a SNP) to a few bases in length. In an embodiment, targeted regions in the genome can be preferentially enriched using hybrid capture probes wherein the hybrid capture probes are shorter than 90 bases, and can be less than 80 bases, less than 70 bases, less than 60 bases, less than 50 bases, less than 40 bases, less than 30 bases, or less than 25 bases. In an embodiment, to increase the chance that the desired allele is sequenced, the length of the probe that is designed to hybridize to the regions flanking the polymorphic allele location can be decreased from above 90 bases, to about 80 bases, or to about 70 bases, or to about 60 bases, or to about 50 bases, or to about 40 bases, or to about 30 bases, or to about 25 bases.

In an embodiment, the hybrid capture probes can be designed such that the region of the capture probe with DNA that is complementary to the DNA found in regions flanking the polymorphic allele is not immediately adjacent to the polymorphic site. Instead, the capture probe can be designed such that the region of the capture probe that is designed to hybridize to the DNA flanking the polymorphic site of the target is separated from the portion of the capture probe that will be in van der Waals contact with the polymorphic site by a small distance that is equivalent in length to one or a small number of bases. In an embodiment, the hybrid capture probe is designed to hybridize to a region that is flanking the polymorphic allele but does not cross it; this may be termed a flanking capture probe. The length of the flanking capture probe may be less than about 120 bases, less than about 110 bases, less than about 100 bases, less than about 90 bases, and can be less than about 80 bases, less than about 70 bases, less than about 60 bases, less than about 50 bases, less than about 40 bases, less than about 30 bases, or less than about 25 bases. The region of the genome that is targeted by the flanking capture probe may be separated by the polymorphic locus by 1, 2, 3, 4, 5, 6, 7, 8, 9, 10, 11-20, or more than 20 base pairs.

For small insertions or deletions, one or more probes that overlap the mutation may be sufficient to capture and sequence fragments comprising the mutation. Hybridization may be less efficient between the probe-limiting capture efficiency, typically designed to the reference genome sequence. To ensure capture of fragments comprising the mutation one could design two probes, one matching the normal allele and one matching the mutant allele. A longer probe may enhance hybridization. Multiple overlapping probes may enhance capture. Finally, placing a probe immediately adjacent to, but not overlapping, the mutation may permit relatively similar capture efficiency of the normal and mutant alleles.

For Short Tandem Repeats (STRs), a probe overlapping these highly variable sites is unlikely to capture the fragment well. To enhance capture a probe could be placed adjacent to, but not overlapping the variable site. The fragment could then be sequenced as normal to reveal the length and composition of the STR.

For large deletions, a series of overlapping probes, a common approach currently used in exon capture systems may work. However, with this approach it may be difficult to determine whether or not an individual is heterozygous. According to the method provided, custom probes are designed to ensure capture of the unique set of somatic mutations identified in the patient's tumor.

A targeted capture based disease screening test could be combined with another targeted capture based non-invasive prenatal diagnostic test, e.g., for aneuploidy.

Capture probes can be modified to comprise purification moieties that serve to isolate the capture duplex from the unhybridized, untargeted cfDNA sequences by binding to a purification moiety binding partner. Suitable binding pairs for use in the invention include, but are not limited to, antigens/antibodies (for example, digoxigenin/antidigoxigenin, dinitrophenyl (DNP)/anti-DNP, dansyl-X-antidansyl, Fluorescein/anti-fluorescein, lucifer yellow/anti-lucifer yellow, and rhodamine anti-rhodamine); biotin/avidin (or biotin/streptavidin); calmodulin binding protein (CBP)/calmodulin; hormone/hormone receptor; lectin/carbohydrate; peptide/cell membrane receptor; protein A/antibody; hapten/antihapten; enzyme/cofactor; and enzyme/substrate. Other suitable binding pairs include polypeptides such as the FLAG-peptide (Hopp et al., BioTechnology, 6:1204-1210 (1988)); the KT3 epitope peptide (Martin et al., Science, 255:192-194 (1992)); tubulin epitope peptide (Skinner et al., J. Biol. Chem., 266: 15163-15166 (1991)); and the T7 gene 10 protein peptide tag (Lutz-Freyermuth et al., Proc. Natl. Acad. Sci. USA, 87:6393-6397 (1990)) and the antibodies each thereto. Further non-limiting examples of binding partners include agonists and antagonists for cell membrane receptors, toxins and venoms, viral epitopes, hormones such as steroids, hormone receptors, peptides, enzymes and other catalytic polypeptides, enzyme substrates, cofactors, drugs including small organic molecule drugs, opiates, opiate receptors, lectins, sugars, saccharides including polysaccharides, proteins, and antibodies including monoclonal antibodies and synthetic antibody fragments, cells, cell membranes and moieties therein including cell membrane receptors, and organelles. In some embodiments, the first binding partner is a reactive moiety, and the second binding partner is a reactive surface that reacts with the reactive moiety, such as described herein with respect to other aspects of the invention. In some embodiments, the oligonucleotide primers are attached to the solid surface prior to initiating the extension reaction. Methods for the addition of binding partners to capture oligonucleotide probes are known in the art, and include addition during (such as by using a modified nucleotide comprising the binding partner) or after synthesis. Additionally, the capture probes can be tethered to a solid surface, e.g., a magnetic bead, which facilitates the isolation of captured sequences.

Synthesis of capture probes can be performed by methods known in the art. For example, in parallel synthesis of capture probes can be obtained using an Agilent microarray that allows for the synthesis of long, e.g., 200-mer, oligonucleotides. Capture probes can be modified during synthesis or following synthesis to comprise moieties that allow for the isolation of the duplex formed by the capture probe while hybridized to the target sequence as described elsewhere herein.

Phase II—Detection and Monitoring Tumors by Analyzing cfDNA

Capturing Somatic Mutations in cfDNA

In the second phase of the method, samples that are used for determining the tumor fraction of the patient include samples that contain nucleic acids that are "cell-free" (e.g., cell-free DNA). Cell-free nucleic acids, including cell-free DNA (cfDNA), can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J. Mol. Diagn. 6: 101-107 [2004]). Other biological fluid samples include, but are not limited to blood, sweat, tears, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can comprise two or more of a biological fluid sample, a tissue sample, and a cell culture sample. As used herein, the terms "blood," "plasma" and "serum" expressly encompass fractions or processed portions thereof.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like. In one illustrative, but non-limiting embodiment, the sample is a blood sample obtained from a cancer patient.

In various embodiments the cfDNA present in the sample can be enriched specifically or non-specifically prior to use (e.g., prior to capture and sequencing). Non-specific enrichment of sample DNA refers to the whole genome amplification of the genomic DNA fragments of the sample that can be used to increase the level of the sample DNA prior to capture and sequencing. Non-specific enrichment can be the selective enrichment of exomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample is unenriched for cfDNA.

As is described elsewhere herein, cfDNA is present as fragments averaging about 170 bp. Accordingly, further fragmentation of cfDNA is not needed. In some embodiments, sufficient cell free DNA is obtained from a 10 ml blood sample to confidently determine the presence or absence of cancer in a patient. The blood samples used in the method provided can be of about 5 ml, about 10 ml, about 15 ml, about 20 ml, about 25 ml or more than 25 ml. Typically, 20 ml of blood plasma contains between 5,000 and 10,000 genome equivalents, and provides more than sufficient cfDNA for determining tumor fraction according to the method provided. In some embodiments, sufficient cfDNA is obtained from 10 ml to 20 ml of blood to determine tumor fraction.

To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, Ind., Qiagen, Germantown, MD).

cfDNA can be end-repaired, and optionally dA tailed, and double-stranded adaptors comprising sequences complementary to amplification and sequencing primers are ligated to the ends of the cfDNA molecules to enable NGS sequencing, e.g., using an Illumina platform. Additionally, each of the double-stranded adaptors further comprises a non-random barcode sequence, which serves to differentiate individual cfDNA molecules. In some embodiments, the barcode sequences are random sequences. In other embodiments, the barcode sequences are non-random barcode sequences. Non-random barcode sequences provide a significant advantage over random barcode sequences because non-random barcode sequences enable unambiguous identification of the sequencing reads described below. The nonrandom barcode sequences are designed specifically to be base-balance both within and across all barcodes. Additionally, in some embodiments, the nonrandom barcodes can comprise a T nucleotide at the 3' end, which is complementary to the A nucleotide of dA-tailed cfDNA molecules. In embodiments utilizing a T nucleotide overhang at the 3' end of the barcode, barcodes of three different lengths can be designed to avoid a single base flashing across the entire flowcell of the sequencer. Nonrandom barcode sequences can be present in adaptors as sequences of 13, 14, and 15 bp; 10, 11, and 12 bp; 11, 12, and 13 bp; 13, 14, and 15 bp; 14, 15, and 16 bp; 15, 16, and 17 bp, and the like. In some embodiments, the shortest barcode sequence can be 8 bp and the longest barcode sequence can be 100 bp. An exemplary set of barcodes having three different lengths is provided in Table 1. Additional barcodes are provided in, for example, U.S. Provisional Application No. 62/348,791, filed 10 Jun. 2016, and U.S. Provisional Application No. 62/364,256, filed 19 Jul. 2016.

TABLE 1

| | Nonrandom barcode sequence |
|---|---|
| SEQ. ID NO: 1 | AATGCCATGGCTT |
| SEQ. ID NO: 2 | CAGTAGCTCTGAT |
| SEQ. ID NO: 3 | GACGTATACGCTT |
| SEQ. ID NO: 4 | TACGGACTCGTAT |
| SEQ. ID NO: 5 | AACGTTCGAGTCCT |
| SEQ. ID NO: 6 | CACGTTACGATGAT |
| SEQ. ID NO: 7 | GCTCCTAGACGTAT |

TABLE 1-continued

| | Nonrandom barcode sequence |
|---|---|
| SEQ. ID NO: 8 | TATCGAGCTAGCCT |
| SEQ. ID NO: 9 | ACGTAGCTGATCAGT |
| SEQ. ID NO: 10 | CAGGACTAGCTTACT |
| SEQ. ID NO: 11 | GCATCGCTAGTAGAT |
| SEQ. ID NO: 12 | TACGTAGTACGCAGT |

Each sequence of the panel that is present in the cfDNA sample is targeted by one or more capture probes described elsewhere herein, and is isolated for further analysis.

Sequencing and Analysis

The barcoded cfDNA fragments isolated form the patient's fluid sample, e.g., blood sample, are amplified, e.g., by PCR, and captured using the hybrid probes. Capturing of the barcoded fragments comprises obtaining single strands of barcoded cfDNA, and hybridizing the barcoded cfDNA with different hybrid probes. Each of the different hybrid probes hybridizes to a single-stranded barcoded cfDNA target sequence to form a target-hybrid probe duplex. The duplex is isolated from unhybridized cfDNA by binding the purification binding moiety comprised in the hybrid probe to the corresponding purification moiety binding partner. As described elsewhere herein, the corresponding purification moiety binding partner can be immobilized on a solid surface, e.g., a magnetic bead, which facilitates the separation of the capture duplex from unhybridized cfDNA molecules in solution. The barcoded cfDNA of the duplex is released, and is subjected to sequencing using an NGS instrument.

In some embodiments, the captured sequences can be analyzed using the sequencing-by-synthesis technology of Illumina, which uses fluorescent reversible terminator deoxyribonucleotides. The reads generated by the sequencing process are aligned to a reference sequence and associated with a sequence of the somatic sequence panel specific for the patient. Mapping of the sequence reads can be achieved by comparing the sequence of the reads with the sequence of the reference genome to determine the specific genetic information, and optionally the chromosomal origin of the sequenced nucleic acid (e.g., cell free DNA) molecule. A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al, Genome Biology 10:R25.1-R25.10 [2009]), or ELAND (Illumina, Inc., San Diego, CA, USA). In one embodiment, the sequencing data is processed by bioinformatic alignment analysis for the Illumina Genome Analyzer, which uses the Efficient Large-Scale Alignment of Nucleotide Databases (ELAND) software. Additional software includes SAMtools (SAMtools, Bioinformatics, 2009, 25(16):2078-9), and the Burroughs-Wheeler block sorting compression procedure which involves block sorting or preprocessing to make compression more efficient.

The error rate in sequencing using NGS methods is of approximately 1 in 500 bases which results in many sequencing errors. The high error rate becomes problematic especially when attempting to identify somatic mutations in mixtures of DNA sequences comprising only a small fraction of mutated species. Additionally, NGS methods typically utilize single stranded DNA as the primary source of sequencing material. Any error included during the amplification step of the DNA molecule prior to sequencing is perpetuated, and becomes indistinguishable as an extraneous technology-dependent mistake. Chemical errors occur at a frequency of approximately in 1000 bases. The combination of sequencing and chemical errors obscure the limit of detection (LOD).

Accordingly, in some embodiments, double-stranded sequencing of the cfDNA is performed. As described elsewhere herein cfDNA can be end-repaired, and optionally dA tailed, and double-stranded adaptors comprising sequences complementary to amplification and sequencing primers are ligated to the ends of the cfDNA molecules to enable NGS sequencing, e.g., using an Illumina platform.

Because every adapter contains a different barcode, every DNA fragment becomes labeled with two distinct barcode sequences (arbitrarily designated A with complementary barcode sequence A', and B with complementary barcode sequence B'. See Figure). Following ligation of the barcoded adaptors to the ds cfDNA molecule, the individually barcoded strands are PCR amplified from asymmetric primer sites on the adaptor tails and subjected to paired-end sequencing using, for example, an Illumina platform. Two species of mate-pair PCR products are produced from each DNA fragment. Those derived from one strand will have the A tag sequence adjacent to flow cell sequence S1 and the B tag sequence adjacent to flow cell sequence S2. Thus, the first strand will contain barcode sequences $A_{R1}|B_{R2}$, and the second strand will contain barcode sequences $B_{R1}|A_{R2}$.

Sequence reads sharing a unique set of tags are grouped into paired families with members having strand barcode identifiers in either the $A_{R1}|B_{R2}$ or $B_{R1}|A_{R2}$ orientation. Each family pair reflects the amplification of one double-stranded DNA fragment. Double-stranded sequencing allows to differentiate true somatic mutations, e.g., substitutions, mutations arising from chemical damage, e.g., during sample preparation, and sequencing errors, and thereby correct for chemical and sequencing errors to maximize the specificity of the assay (FIG. 9). Only true mutations present on both strands of a DNA fragment will appear in all members of a family pair. The tumor fraction can then be calculated as the proportion of different cfDNA sequences each comprising at least one somatic mutation, i.e., ctDNA sequences, relative to the total number of different cfDNA, i.e., ctDNA and corresponding normal sequences. Unlike the single-stranded approach, the current method corrects for random sequencing errors.

In some embodiments, at least 10 different somatic mutations, at least 20 different somatic mutations, at least 30 different somatic mutations, at least 40 different somatic mutations, at least 50 different somatic mutations, at least 60 different somatic mutations, at least 70 different somatic mutations, at least 80 different somatic mutations, at least 100 different somatic mutations, at least 150 different somatic mutations, at least 200 different somatic mutations, at least 250 different somatic mutations, at least 300 different somatic mutations, at least 400 different somatic mutations, at least 500 different somatic mutations, or more than 500 different mutants are identified in the cfDNA sample from the patient. The number of segregating markers that can theoretically be identified in a sample may be up to the number of unique segregating markers between the nucleic acid specimens being tested. For example, there are about 3 million segregating markers between two individual humans, while the number for a tumor sample may differ from a matched non-tumor sample from the patient may have 10, 100, 1000, 10,000 or more markers. In some embodiments, the different mutants are identified at a molecular depth of at least 1,000, at least 2,000, at least 3000, at least 4,000, at least 5,000, at least 6,000, at least 7,000, at least 8,000, at least 9,000, at least 10,000 or more. In other embodiments, the different mutations are identified at a sequencing depth of up to the total amount of nucleic acid molecules present in the sample.

In some embodiments, the mutations are germ-line mutations. In some embodiments the mutations are somatic mutations.

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Computer Simulation of Determination of Tumor Fraction

This example is of a computer simulation of an experiment designed to determine the tumor fraction according to the methods provided herein.

In this example, we assumed a panel of 100 somatic sites were interrogated at a depth of 5000-fold in a virtual sample, i.e., in silico, having a tumor fraction of 1e−4. 100,000 repetitions of the process were performed, and the number of tumor molecules were scored in each case.

Targeting 100 somatic sites, and sequencing the sites at a depth of 5e3, given a tumor fraction of 1e−4, one would expect to see about 50 tumor molecules in a background of 500,000 normal molecules. Each repetition begins with zero tumor reads. Each site is then scored as yielding some number of tumor reads (potentially zero or more) by the use of a random draw from a binomial distribution with a probability of success equal to 1e−4 and the number of trials equal to 5000.

Figure 2:
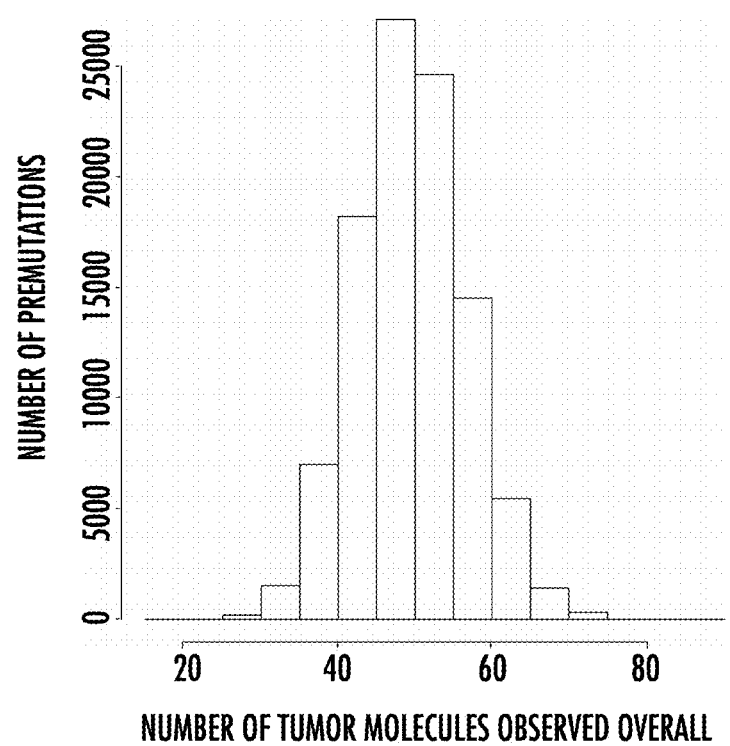
FIG. 2 illustrates the results of a computer simulated experiment for determining the number of tumor molecules in a sample having between 3000-5000 copies of a genome. Reference is made to Example 1.

For example, the first run of the simulation would begin with zero tumor reads. Then for site 1 a single random draw from a bionomial distribution with the above criteria is made, and this amount is added to the tumor tally. Then for site 2 another single random draw from the bionomial distribution is made, and that amount is also added to the tumor tally. This is repeated for each site until all sites are "tested". This process is repeated 100,000 times. The results are shown in FIG. 2, which is a histogram of tumor reads per permutation over the 100,000 permutations.

The sensitivity of the method as determine by this simulation shows that we can expect the detection of at least 20 tumor molecules, i.e., molecules comprising somatic sites, in a total background of 500,000 normal molecules, i.e., sites that were not detected to contain a somatic mutation of the panel. The simulation shown in FIG. 2 is based on the detection of somatic mutations in cell free DNA from a plasma sample from a blood draw of about 20 ml, which is estimated to contain between 3000-5000 genome copies. Targeting 100 somatic sites, and sequencing the sites at a depth of 5e3, given a tumor fraction of 1e−4, one would expect to see about 50 tumor molecules in a background of 500,000 normal molecules. Given these conditions, the distribution of the number of tumor molecules observed in 100,000 simulations of the process, i.e., experiment, detected at least 20 tumor molecules in all simulations. Thus, the method provides for extremely high sensitivity.

Figure 3:
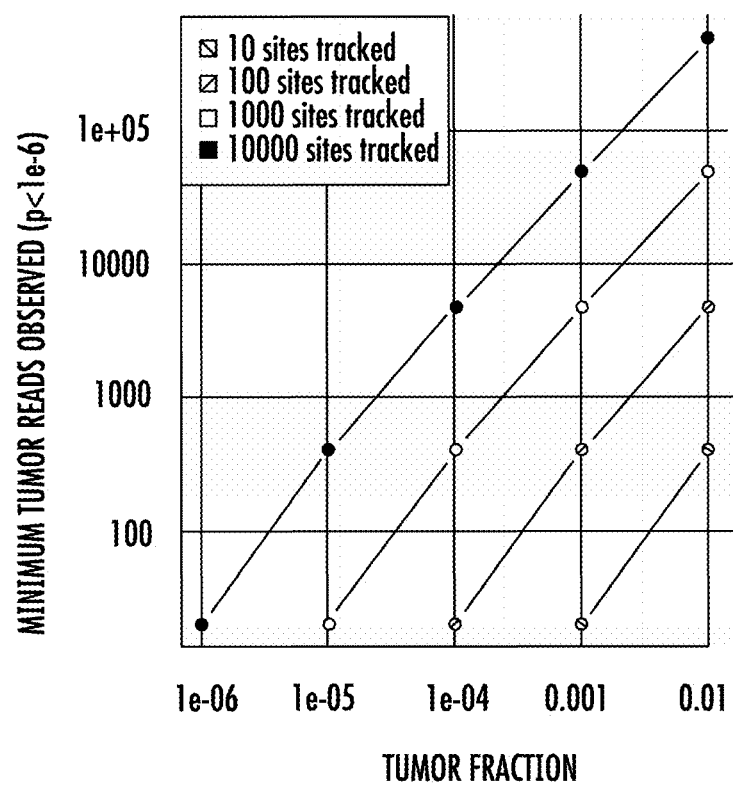
FIG. 3 illustrates the relationship between number of tumor reads observed and the nucleic acid sample's tumor fraction. Reference is made to Example 1.

FIG. 3 illustrates this same simulation procedure for determining the minimum number of reads that will be observed under different conditions, e.g., different number of sites that are tracked, and different levels of tumor fraction. The graph shows different lines representing the different number of sites tracked, and the minimum number of reads observed at a given tumor fraction. The minimum value for number of tumor reads is 20 for each plot line. However, differing conditions will produce different plots where the minimum value may be larger (or smaller) than 20; a histogram generated by a simulation, with specified parameters (tumor fraction, number of sites), will look similar to the histograms in FIG. 3 but shifted along either axis. For example, tracking 1000 sites at a tumor fraction of 1 in 10,000, one observes about 600 tumor sites. Extrapolating, if 3e6 sites are tracked (i.e., the number of genetic differences between two humans), then it is expected that the assay could detect the presence of one human sample amongst random DNA if the human was present at a proportion of 3e−8. (which is 1/(#sites*100)). The greater the number of sites, the smaller the tumor fraction needed to detect the presence of somatic, i.e., cancer mutations. Current methods used by others typically detect somatic mutations at tumor fractions of 1 in 100 or 1 in a 1000. The method provided herein detects somatic mutations at tumor fractions that are 10 to 1000 fold lower than fractions required by methods of others.

Although this example has been written for a tumor it is equally applicable to a mixture of any two nucleic acid sequence populations from more than one source, e.g., two different humans. Thus, it is applicable for distinguishing between fetal and maternal nucleic acids, distinguishing between a host and an infectious agent, distinguishing between between crops, determining the presence of a single individual's nucleic acid sequence in a mixture of nucleic acid sequences.

Example 2

Detection of Somatic Mutations in Mixtures of Homozygous and Heterozygous Sequences Derived from a Mixture of Two Samples The purpose of this experiment was to assess the ability of the method provided to detect very small mixtures of DNA, on the order of 1 foreign molecule per 1 million "background" molecules, by mixing DNA from two donor samples in known proportions and sequencing it as described.

Method
1. Extract genomic DNA from two donor samples. Prepare library for each donor that contains molecular barcodes that allow for duplex sequencing, and sample barcode sequences that indicate which sample downstream sequencing reads originated from.
2. Whole-genome sequence the two samples.
3. Select ~10,000 sites that are homozygous in Sample 1 and heterozygous in Sample 2. Sample 2 was considered as the "cancer" sample.
4. Design and synthesize biotinylated hybrid capture probes targeting those 10,000 sites to enrich for sites containing segregating markers.

5. Make mixtures of Sample 2 DNA into Sample 1 DNA at a variety of mixture proportions:
   a. 1e−2
   b. 1e−3
   c. 1e−4
   d. 1e−5
   e. 1e−6
   f. 0 (negative control)
6. Sequence mixed samples using a duplex sequencing workflow and enriched using hybrid capture probes that were designed in step 4.
7. Analyze sequence data:
   a. Align to human genome
   b. Collapse molecular barcodes into reads/molecules
   c. Filter out noisy sites heuristically, taking into account molecular barcodes and observed reads in the negative control sample.
   d. Tally/count observed cancer reads and observed non-cancer reads
   e. Compute estimated tumor fraction.
8. Compare estimates to expected mixtures.

Figure 4:
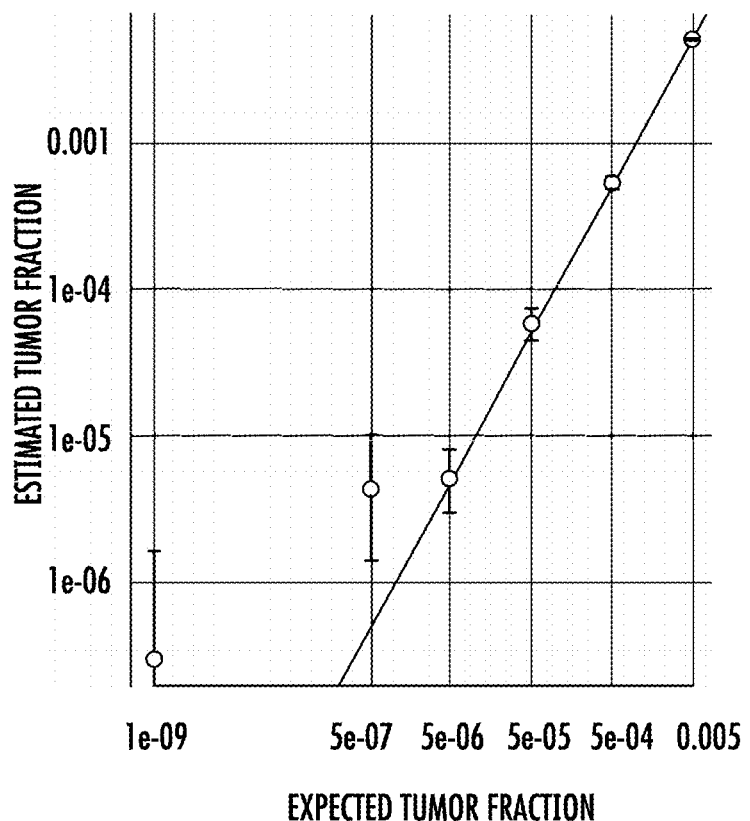
FIG. 4 shows a graph illustrating the significant level of detection of somatic mutations in a sample comprising increasingly diluted "cancer" sequences. Reference is made to Example 2.
Figure 5A:
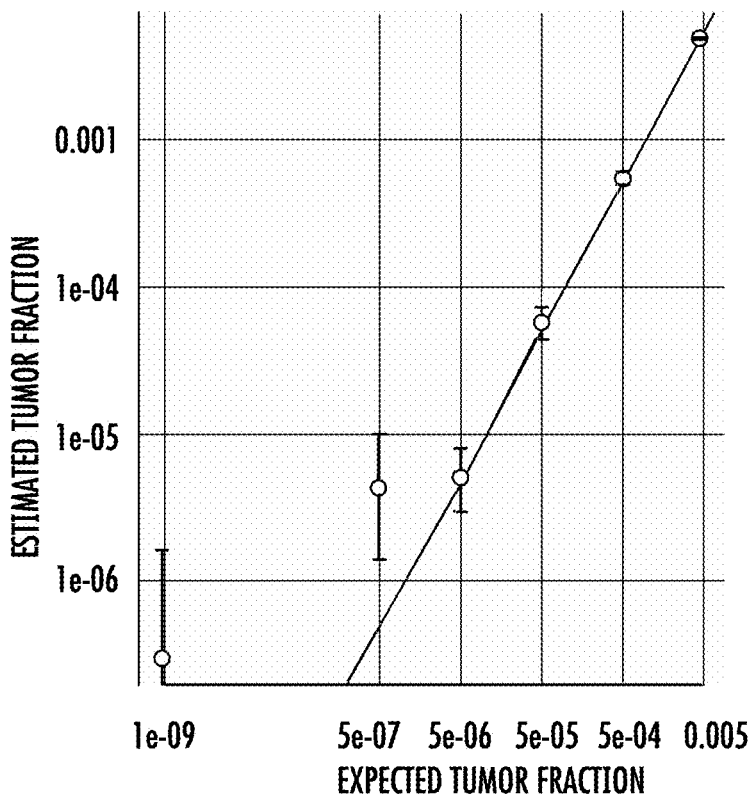
FIGS. 5A-C show in (A) the graph provided in FIG. 4, and the number of reads normal reads (B) and cancer reads (C) obtained for the conditions described for the previous plot. Reference is made to Example 2.
Figure 5B:
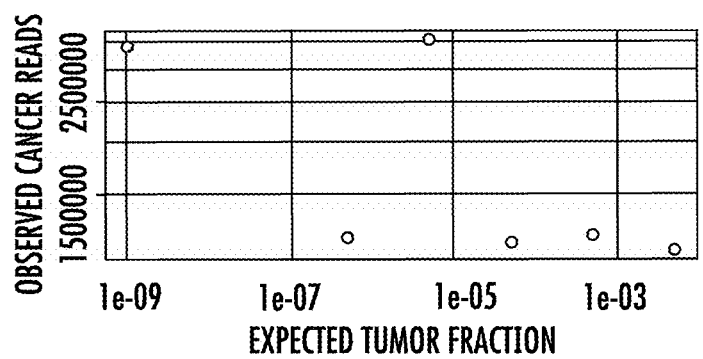
Figure 5C:
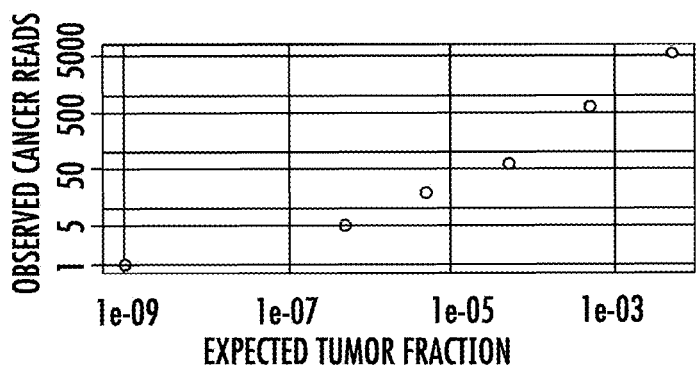

The results are shown in FIGS. 4, 5 and 6. The results provided in FIG. 4 show that detection of as low as 5 tumor molecules per 1,000,000 molecules sequenced was obtained. In the graph, each point is the tumor fraction expected to be seen (X-axis), and the observed tumor fraction (Y-axis). The 1e−9 data point is the zero fraction. Notably, the error bars at the tumor fractions, e.g., at 5e−6, do not overlap with the error bars of the zero fraction. Thus the method accurately detect and quantifies tumor in a mixture having a fraction as low as 5 molecules per 1,000,000 molecules when sequencing 10,000 sites in the panel. Note: expected tumor fraction is 0.5*experimental mixture proportion, due to mostly heterozygous sites being chosen in the initial test sample (step 3).

Statistically significant detection was achieved for mixtures down to 5 parts per million, compared to a negative control. Statistical power to detect mixtures is driven by plasma sequencing depth and number of sites tracked.

FIG. 5 shows in (A) the graph provided in FIG. 4, and the number of reads normal reads (B) and cancer reads (C) obtained for the conditions described for the previous plot.

FIG. 6 shows a table of the results obtained for the 5:1,000,000 and the zero condition. 18 cancer reads were detected out of 3,540,529 normal reads, which gives an estimated cancer proportion of 18/3,540,529=5.0840e−6 with a 95% binomial confidence interval around the estimate. The statistical significance is that the positive condition and the negative condition do not overlap.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 3

Clinical Samples

This example discloses the test on three different patient samples

Samples were obtained from a commercial sample acquisition company. The samples were as follows:

TABLE 2

| Patient | Type and Stage | Samples Available | Somatic Mutations Identified |
|---|---|---|---|
| 1067 | Stage 3c Breast | FFPE Tumor, Fresh-Frozen Tumor, Normal, Pre-Op Plasma | 562 |
| 1071 | Stage 3a Lung Squamous Cell Carcinoma | FFPE Tumor, Fresh-Frozen Tumor, Normal, Pre-Op Plasma | 3575 |
| 2956 | Stage 1a Lung Adenocarcinoma | FFPE Tumor, Normal, Pre-Op Plasma, Post-Op Plasma | 47 |

Figure 7A:
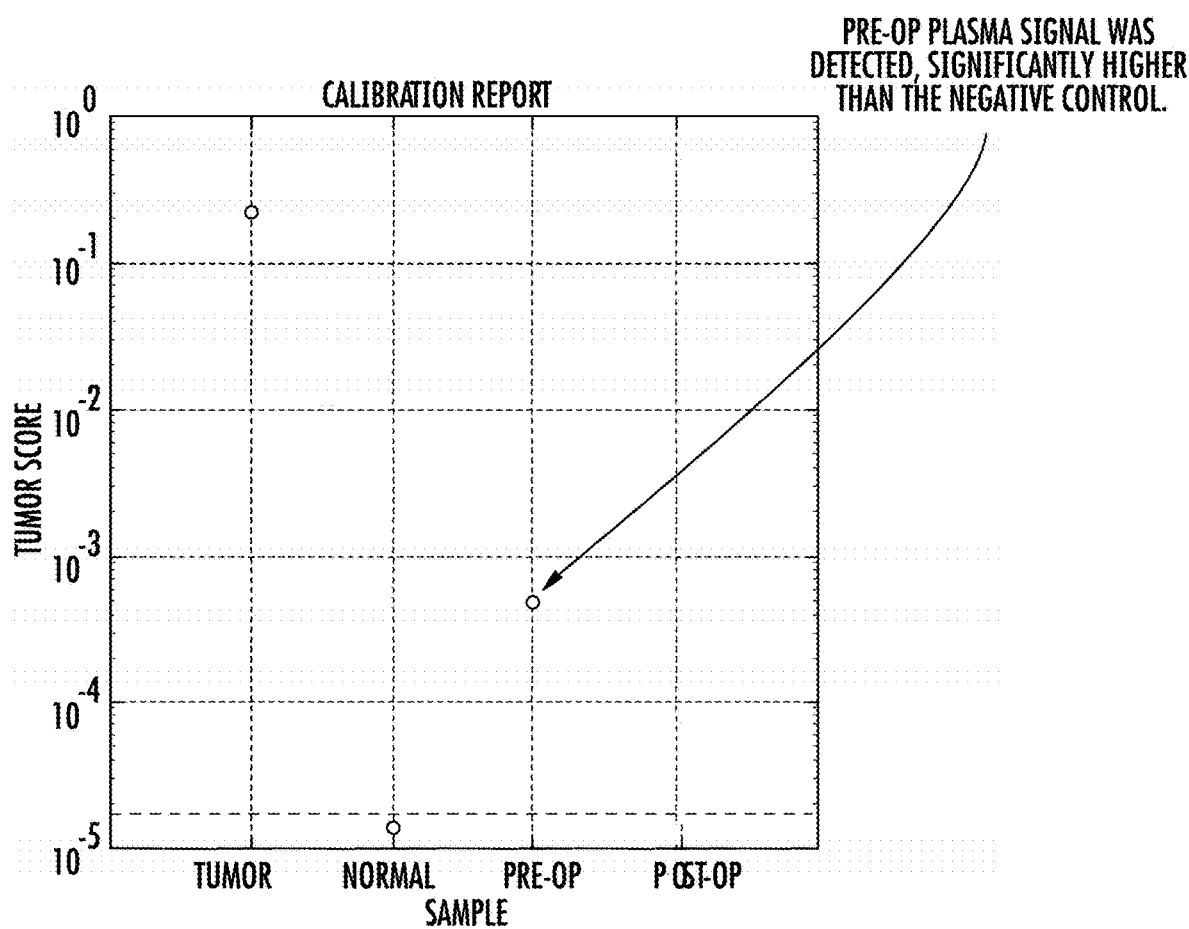
FIGS. 7A-7C are graphs summarizing the results of Example 3.
Figure 7B:
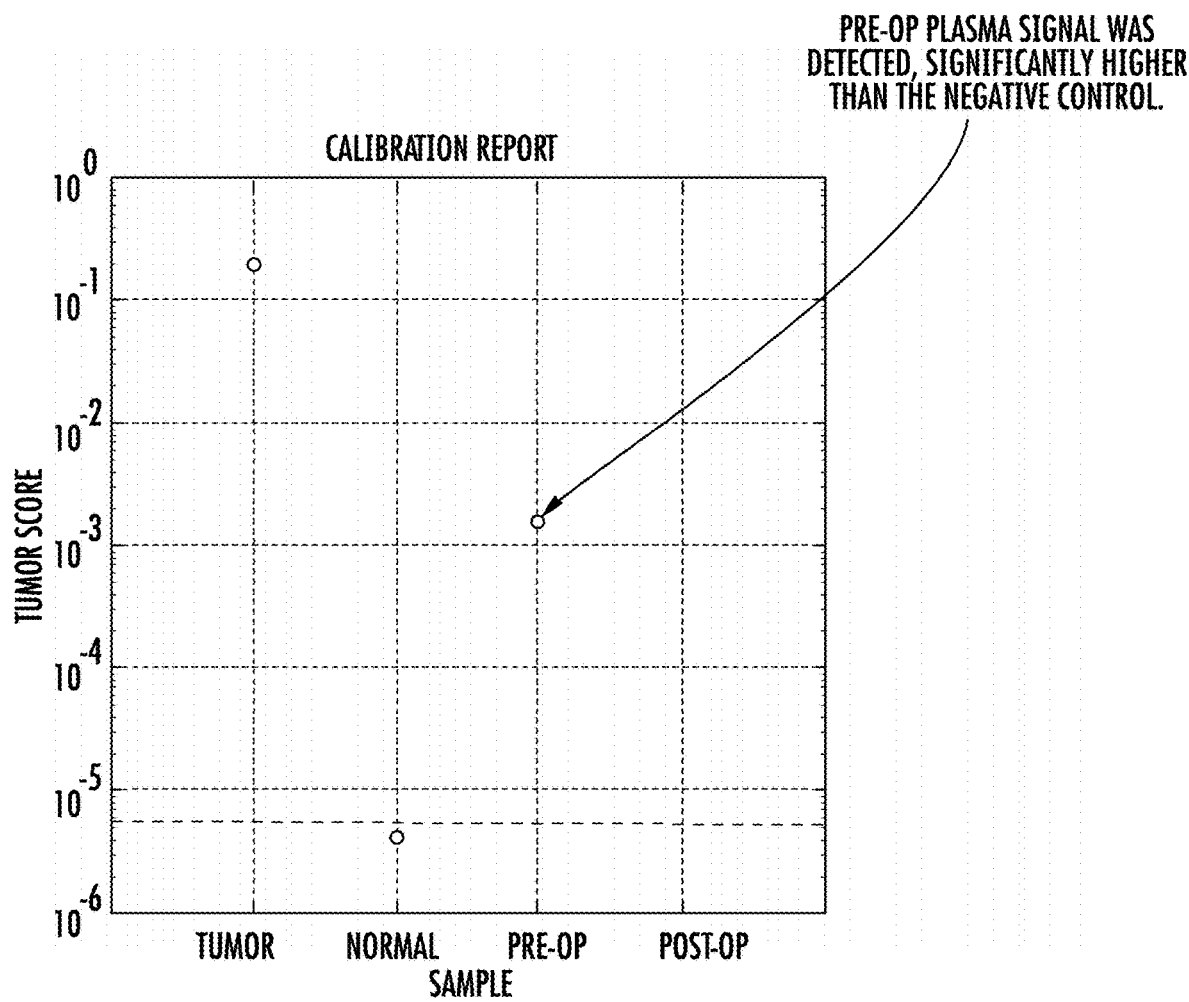
Figure 7C:
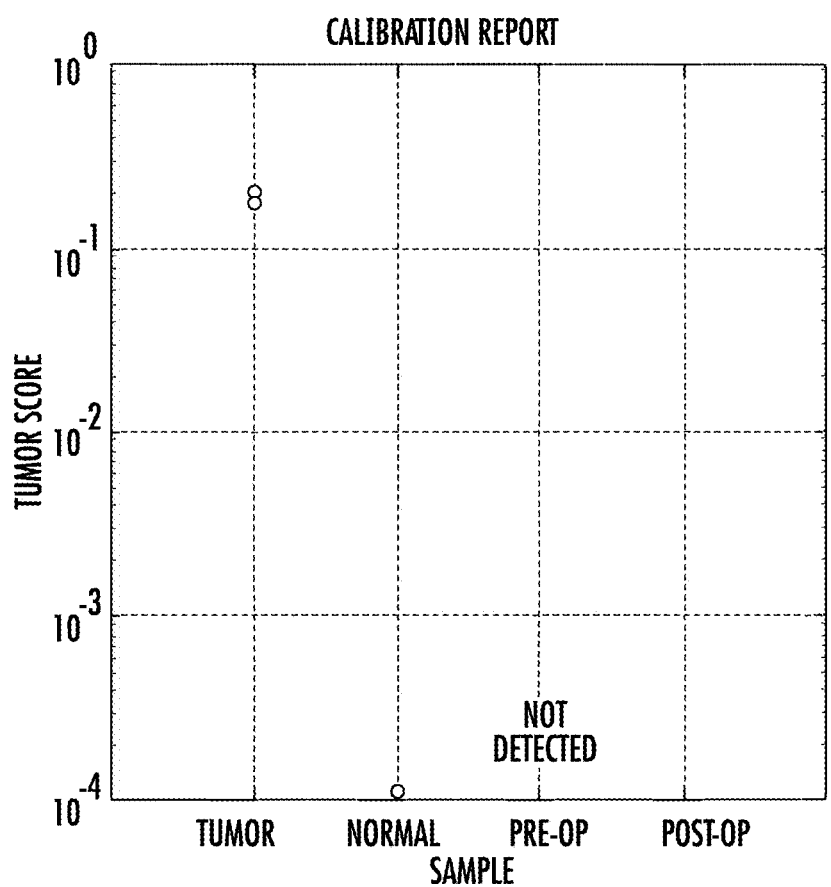

The samples were characterized as described herein. Tumor and normal samples were subjected to whole genome sequencing and the somatic mutations were identified. Next, hybrid capture probes were designed targeting all somatic mutations identified for the respective sample. For example, patient 1067 had 562 probes designed for each of the 562 somatic mutations identified. All samples (tumor, normal, cfDNA from plasma) for each patient were re-sequenced using the designed probes and a duplex sequencing workflow to eliminate biological and systemic noise introduced in the workflow. The results are shown in FIG. 7A-C. As can be seen each of the Stage 3 cancers were detectable in the tumor and pre-op plasma indicating that it is possible to design probes capable of detecting the mutations in nucleic acid.

The Stage 1 sample (Sample 2956) did not provide a signal in the pre-op plasma indicating that the level of tumor cfDNA was below the limit of detection. This indicated that there were insufficient markers to enable detection of the cancer in this plasma sample. However, identifying more segregating markers may provide a detectable signal.

It is understood that the examples and embodiments described herein are for illustrative purposes only and that various modifications or changes in light thereof will be suggested to persons skilled in the art and are to be included within the spirit and purview of this application and scope of the appended claims. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for preparing a deoxyribonucleic acid (DNA)-enriched fraction from a cancer patient, comprising:
   (a) obtaining a tumor sample and a non-tumor sample from the cancer patient;
   (b) sequencing genomic DNA from the tumor sample and sequencing genomic DNA from the non-tumor sample, thereby obtaining sequences of genomic DNA from the tumor sample and sequences of genomic DNA from the non-tumor sample;

(c) aligning the sequences of genomic DNA from the tumor sample to a reference human genome that is not from the patient thereby obtaining a set of tumor-specific mutations and further obtaining from the set of tumor-specific mutations a set of tumor-specific somatic mutation sequences that are present in the sequences of genomic DNA from the tumor sample but not present in the sequences of genomic DNA from the non-tumor sample;

(d) extracting cell-free DNA fragments (cfDNA) from a substantially cell-free fluid sample of blood plasma or blood serum obtained from the cancer patient;

(e) contacting the extracted cfDNA fragments with a plurality of oligonucleotides, wherein each oligonucleotide in the plurality of oligonucleotides comprises a nucleic acid sequence that is capable of hybridizing to a DNA fragment comprising one of the set of tumor-specific somatic mutation sequences; and (f) enriching a fraction of DNA corresponding to the set of tumor-specific somatic mutation sequences from the extracted cfDNA fragments by:
  (i) hybrid capture-based enrichment;
  (ii) PCR-target enrichment; or
  (iii) on-sequencer enrichment.

2. The method of claim 1, wherein the method comprises a detection sensitivity of about 20 to about 50 ctDNA fragments comprising one or more of the set of somatic mutations in the fluid sample per a total background of about 500,000 cfDNA fragments.

3. The method of claim 1, wherein the plurality of oligonucleotides is capable of detecting at least 10 different tumor-specific somatic mutations.

4. The method of claim 1 further comprising sequencing one or more of the DNA fragments.

5. The method of claim 1, wherein extracting cfDNA fragments from the substantially cell-free fluid sample of blood plasma or blood serum comprises separating cfDNA from the blood plasma or blood serum sample.

6. The method of claim 1, wherein the cancer patient has a cancer selected from adrenal cancer, anal cancer, bile duct cancer, bladder cancer, bone cancer, a brain/CNS tumor, breast cancer, Castleman disease, cervical cancer, colon or rectum cancer, endometrial cancer, esophagus cancer, a Ewing tumor, eye cancer, gallbladder cancer, a gastrointestinal carcinoid tumor, a gastrointestinal stromal tumor (GIST), gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic Syndrome, nasal cavity or paranasal sinus cancer, nasopharyngeal cancer, neuroblastoma, oral cavity or oropharyngeal cancer, osteosarcoma, ovarian cancer, pancreatic cancer, penile cancer, a pituitary tumor, prostate cancer, retinoblastoma, rhabdomyosarcoma, salivary gland cancer, skin cancer, small intestine cancer, stomach cancer, testicular cancer, thymus cancer, thyroid cancer, uterine sarcoma, vaginal cancer, vulvar cancer, Waldenstrom macroglobulinemia, and Wilms tumor.

7. The method of claim 1, wherein the plurality of oligonucleotides is capable of detecting at least 50 different tumor-specific somatic mutations.

8. The method of claim 1, wherein the plurality of oligonucleotides is capable of detecting at least 500 different tumor-specific somatic mutations.

9. The method of claim 1, wherein sequencing genomic DNA from the tumor sample of the patient and sequencing genomic DNA from the non-tumor sample of the patient comprises whole genome sequencing.

10. The method of claim 1, wherein sequencing genomic DNA from the tumor sample of the patient and sequencing genomic DNA from the non-tumor sample of the patient comprises targeted sequencing.

11. The method of claim 10, wherein the targeted sequencing comprises sequencing introns, exons, or a combination thereof.

12. The method of claim 1, wherein (d)-(f) are repeated one or more times following completion of a cancer treatment.

13. The method of claim 1, where wherein (d)-(f) are repeated one or more times while the cancer patient is in remission.

14. The method of claim 1, where wherein (d)-(f) are repeated one or more times coinciding with or prior to surgery; following, during, or prior to administration of chemotherapy; or following, during, or prior to radiation therapy.

* * * * *